(12) United States Patent
Welt et al.

(10) Patent No.: US 10,227,419 B2
(45) Date of Patent: *Mar. 12, 2019

(54) ANTIBODIES TARGETING B-CELL RECEPTOR COMPLEX MEMBRANE BOUND IGM AND USES THEREOF

(71) Applicant: Welt Bio-Molecular Pharmaceutlical, LLC, Armonk, NY (US)

(72) Inventors: Sydney Welt, Armonk, NY (US); David Kostyal, Akron, OH (US); Rachel S Welt, Armonk, NY (US); Virginia Raymond, Armonk, NY (US); Jonathan A Welt, Armonk, NY (US)

(73) Assignee: Welt Bio-Molecular Pharmaceutical, LLC., Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,386

(22) Filed: Feb. 13, 2018

(65) Prior Publication Data

US 2018/0186895 A1 Jul. 5, 2018

Related U.S. Application Data

(63) Continuation of application No. 15/101,658, filed as application No. PCT/US2014/067957 on Dec. 1, 2014, now Pat. No. 9,926,381.

(60) Provisional application No. 61/911,186, filed on Dec. 3, 2013.

(51) Int. Cl.
| | |
|---|---|
| *A61K 39/395* | (2006.01) |
| *A61K 39/40* | (2006.01) |
| *C12P 21/06* | (2006.01) |
| *C07K 16/42* | (2006.01) |
| *C12N 5/16* | (2006.01) |
| *C07K 16/00* | (2006.01) |
| *C07K 16/28* | (2006.01) |

(52) U.S. Cl.
CPC .......... *C07K 16/4283* (2013.01); *C12N 5/163* (2013.01); *C07K 16/2803* (2013.01); *C07K 2317/14* (2013.01); *C07K 2317/34* (2013.01); *C07K 2317/56* (2013.01); *C07K 2317/565* (2013.01); *C07K 2317/73* (2013.01); *C07K 2317/732* (2013.01); *C07K 2317/76* (2013.01); *C07K 2317/77* (2013.01)

(58) Field of Classification Search
None
See application file for complete search history.

(56) References Cited

U.S. PATENT DOCUMENTS

2009/0220416 A1   9/2009   Welt et al.

FOREIGN PATENT DOCUMENTS

| JP | H05503687 A | 6/1993 |
| JP | 2009536217 A | 10/2009 |
| WO | WO 91/04005 | 4/1991 |

OTHER PUBLICATIONS

Denis: "In Vivo Study of migM and migD 1-15 Cross-Linking on Murine B Cells", Scand. J. Immunol., vol. 39, No. 6, Jun. 1, 1994 (Jun. 1, 1994), pp. 625-632.
S. M. Rudich et al: "Anti-IgM-mediated B 1-15 cell signaling. Molecular analysis of ligand binding requisites for human B cell clonal expansion and tolerance", The Journal of Experimental Medicine, vol. 168, No. 1, Jul. 1, 1988 (Jul. 1, 1988), pp. 247-266.
Racine, et al., IgM producton by marrow plasmablasts contributes to long-term protection against intracellular bacterial infection. J Immunol. 2011, 186(2): 1011-21; Abstract, p. 1109, col. 2.
De Pascalis et al., "Grafting of "Abbreviated" Complementarity-Determining Regions Containing Specificity-Determining Residues Essential for Ligand Contact to Engineer a Less lmmunogenic Humanized Monoclonal Antibody", The Journal of Immunology, 2002, 169: 3076-3084.
Maccallum et al., "Antibody-antigen Interactions: Contact Analysis and Binding Site Topography", J. Mo/. Biol. (1 996) 262, t al., "Antibody-antigen Interactions: Contact Analysis and Binding Site Topography", J. Mo/. Biol. (1 996) 262, 732-745.
Xin et al.,"Hybridoma Passage in Vitro May Result in Reduced Ability of Antimannan Antibody to Protect against Disseminated Candidiasis ", Infection and Immunity, Jul. 2006, p. 4310-4321.
Japanese Office Action dated Sep. 25, 2018 in corresponding Japanese Application No. 2016-533109.

*Primary Examiner* — Chun W Dahle
(74) *Attorney, Agent, or Firm* — Leason Ellis LLP

(57) ABSTRACT

The present invention relates to antibodies targeting the membrane bound IgM (mIgM) of the B-cell receptor complex found in B-cell lymphomas and leukemias and uses thereof. Another aspect of the present invention is the use of anti-B-Cell mIgM antibodies in the treatment of Be-cell malignancies, including B-cell lymphomas and leukemias.

7 Claims, 7 Drawing Sheets

Specification includes a Sequence Listing.

ANTIBODIES TARGETING B-CELL RECEPTOR COMPLEX MEMBRANE BOUND IGM AND USES THEREOF

CROSS-REFERENCE TO RELATED PATENT APPLICATIONS

This application is a Continuation of U.S. application Ser. No. 15/101,658, filed Jun. 2, 2016, which is a U.S. National Phase Application under 35 U.S.C. § 371 of International Patent Application No. PCT/US2014/067957, filed Dec. 1, 2014, and claims the benefit of priority under 35 U.S.C. Section 119(e) of U.S. Application Ser. No. 61/911,186, filed Dec. 3, 2013, all of which are incorporated by reference in their entireties. The International Application was published on Jun. 11, 2015 as International Publication No. WO 2015/084736 A2.

GOVERNMENT RIGHTS

This invention was made in part using government support under SBIR Grant No. 1 R43 AI081332-01A1 awarded by the National Institutes of Health. The government has certain rights to this invention.

SEQUENCE LISTING

The instant application contains a Sequence Listing which has been submitted electronically in ASCII format and is hereby incorporated by reference in its entirety. Said ASCII copy, created on Dec. 1, 2014, is named 10199-003571-WO0_SL.txt and is 7,207 bytes in size.

FIELD OF THE INVENTION

The present invention relates to antibodies targeting the membrane bound IgM (mIgM) of the B-cell Receptor Complex found in B-cell lymphomas and leukemias and uses thereof.

BACKGROUND OF THE INVENTION

B-cell malignancies comprise the major subtype of lymphomas today with over 100,000 new cases per year. The vast majority of patients are not curable despite the apparent sensitivity of these diseases to a number of drugs and biologic agents commonly in use. A characteristic of many B-cell lymphomas and leukemias is that chemotherapy and/or biologic based responses are readily obtainable, but cures are more difficult. B-cell lymphoma can be a very aggressive disease where many of the patients do not respond to conventional treatment. It is apparent that residual clones of neoplastic cells remain after log cell kill with chemotherapy and/or biologic therapies. The ability to cure these diseases will be dependent on the success of eradication of all tumor cells, especially tumor stem cells.

Anti-CD20 antibodies such as rituximab, ofatumumab, obinutuzumab, and tositumomab, have also been used to treat B-cell derived malignancies as single agents, as potentiators of chemotherapy, as maintenance therapy and as vehicles to deliver radioisotopes/drugs. These antibodies bind to CD20, a restricted B-cell differentiation antigen expressed only by normal and malignant B-cells. Because of the expression of CD20 antigen on both normal and malignant B-cells, anti-CD20 antibodies can also lead to the destruction of a portion of normal B-cells, the long term consequences of which are unknown. (See, Smith M R, Oncogene 22:7359-7368 (2003); Jacobs S A, et al., Expert Opin Bio Ther 7:1749-1762, (2007)).

In contrast to CD20, the B-cell Receptor Complex (BCRC) is the central differentiation signaling element of the B-cell arm of the immune system and this molecule is expressed on the surface of all B-cell malignancies. The BCRC comprises a cell-surface membrane bound Ig (mIg) (such as mIgM, mIgG, mIgA, mIgE and mIgD) and a closely associated co-signaling molecule CD79αβ. Previous strategies to target the BCRC molecules in B-cell malignancies have focused on the unique CDR sequences specific for each monoclonal tumor. (See, Miller R A, et al., N Engl J Med 306:517, (1982); Levy R, et al., J Natl Cancer Inst Monographs 10:61 (1990); Davis T A, et al., Blood 92:1184-1190 (1998)). However, as a consequence of the uniqueness of each CDR, this approach necessitated the generation of a specific drug for each patient, which proved not to be feasible in the clinic. These early clinical studies targeting the BCRC did, however, demonstrate anti-tumor activity.

The B-cell Receptor (BCR) initiates a driver pathway in B-cell lymphoma-leukemia. One strategy has been to target BCRC associated cytoplasmic molecules such as the Syk tyrosine kinase, a downstream mediator of the BCRC signaling pathway, to inhibit downstream pathway tyrosine kinases. Both vertical and horizontal membrane BCRC interactions render this downstream pathway complex and redundant. As the Syk tyrosine kinase pathway is not restricted to B-cell lineage tissue, its inhibition leads to unwanted immune effects, possible pro-oncogenic effects in breast tissue and other toxicities in non-hematopoietic cells. Further downstream of the BCRC is the Bruton tyrosine kinase (BTK). Bruton tyrosine kinase inhibition has also emerged as a compelling target downstream of the BCR, which is now an approved strategy through the utilization of the drug ibrutinib. The approval of ibrutinib, the first BTK inhibitor demonstrating potent activity, provides compelling evidence of the significance of the BCRC in driving B-cell malignancies. Additional molecular targets have been identified downstream of the BCRC, such as PI3K delta and BCL2, and drugs blocking the activity of these targets are also shown to have significant clinical activity.

As a consequence of the BCR's sequence homology to serum Ig, developing specific anti-membrane Ig therapy was a hurdle. Specific mIgM targeting in vivo was thought not to be feasible, as the drug or biologic would bind to the circulating IgM in blood prior to reaching the cell surface B-cell membrane mIgM. A unique set of sequences previously identified in the membrane-bound Igs, designated proximal domains (PDs), are not expressed in serum Igs. These PDs are Ig class specific and for mIgM constitutes a 13 amino acid peptide. However, attempts to produce anti-mIgM PD antibodies were not successful due to the low immunogenicity of the PD peptide, its hydrophobicity, and the resultant low affinity of the generated antibodies. In contrast, efforts to produce mIgE PD have resulted in several functionally distinct versions. See, e.g., U.S. Pat. No. 8,137,670; U.S. Pat. No. 8,404,236; Poggianella M, et al., J Immunol. 177:3597-3605 (2006); Feichter S, et al., J Immunol 5499-5505 (2008).

There is a need for antibodies that have a high level of specificity for B-cell mIgM in order to internalize the receptor, inhibit cell growth, induce apoptosis or deliver drugs, toxins or radioisotopes to these mIgM B-cells, while sparing normal lymphocytes (non-mIgM expressing B-cells) and non-lymphatic tissues from toxicity. Such antibodies can also be used in diagnostics of B-cell lymphomas and B-cell leukemias. These uniquely specific antibodies will allow for the first time the ability to separate membrane IgM from serum IgM by immune-affinity methodology.

BRIEF DESCRIPTION OF THE FIGURES

FIG. 1A is a micrograph showing the control-IgG2b isotype matched control antibody plus secondary goat anti-mouse Ig-gold. FIGS. 1B and 1C are micrographs showing monoclonal antibody mAb4-2b (hereinafter "mAb 4") binding to 2 different cells of CRL 1648 at the same magnification as the control antibody in FIG. 1A. FIG. 1D is a micrograph showing monoclonal antibody mAb 4 binding to a third CRL 1648 cell at a higher magnification compared to the control antibody of FIG. 1A. Bright white spots represent immune gold particles-goat anti-mouse Ig reacting with the mAb 4 monoclonal antibody on the cell surface.

FIG. 2A is a micrograph showing monoclonal antibody mAb 4 binding to a glutaraldehyde fixed CRL 1648 cell. FIG. 2B is a micrograph showing micro-clusters of BCRC. FIG. 2C is a micrograph showing that when CRL 1648 cells were incubated with mAb 4 at 37° C. for 30 minutes, then fixed and stained with goat-anti-mouse Ig, there was a lack of detectable monoclonal antibody mAb 4 on the membrane due to BCRC internalization. FIG. 2D is a micrograph showing that when CRL 1648 cells were incubated with mAb 4 at 37° C. for 15 minutes, then fixed and stained with goat-anti-mouse Ig, residual bound monoclonal antibody mAb 4 was seen because internalization was incomplete. FIG. 2E is a micrograph showing that when CRL 1648 cells were incubated with monoclonal antibody mAb 4 at 37° C. for 30 minutes, then fixed and stained with goat-anti-hu-IgM, BCRC is not detectable.

FIG. 3 is a micrograph in which monoclonal antibody mAb 4 binding is represented by gold particles-goat-anti-mouse Ig reactivity, demonstrating specific binding to long projections as well as the cell surface of CRL 1596.

FIG. 4A is a micrograph providing a high magnification view of a dense micro-cluster that shows specific binding of monoclonal antibody mAb 4, represented by gold particles-goat-anti-mouse Ig reactivity, to CRL 2260. FIG. 4B is a micrograph providing a topographic view of the same field in FIG. 4A that shows specific binding of monoclonal antibody mAb 4, represented by gold particles-goat-anti-mouse Ig reactivity, to CRL 2260, Diffuse mixed B-cell Lymphoma.

FIG. 5A is a micrograph providing a high magnification view of a dense micro-cluster that shows specific binding of monoclonal antibody mAb 4, represented by gold particles-goat-anti-mouse Ig reactivity, in deep clefts of CRL 3006. FIG. 5B is a micrograph providing a topographic view of the same field in FIG. 5A that shows specific binding of monoclonal antibody mAb 4, represented by gold particles-goat-anti-mouse Ig reactivity, to CRL 3006, Mantle Cell Lymphoma.

FIG. 6A is a graph comparing the effect of monoclonal antibody mAb 4 versus an isotype-matched control antibody on inhibiting growth of mIgM-expressing B-cell line CRL 1648 (CRL 1648 Mκ) (Burkitt's lymphoma). FIG. 6B is a graph comparing the effect of monoclonal antibody mAb2-2b (hereinafter "mAb 2") versus an isotype-matched control antibody on inhibiting growth of mIgM-expressing B-cell line CRL 1648 (CRL 1648 Mκ). FIG. 6C is a graph comparing the effect of monoclonal antibody mAb 4 versus an isotype-matched control antibody on inhibiting growth of control B-cell line expressing mIgG, CRL 2632 (CRL 2632 $G_K$) (Diffuse large cell lymphoma). FIG. 6D is a graph comparing the effect of monoclonal antibody mAb 4 versus an isotype-matched control antibody on inhibiting growth of mIgM-expressing B-cell line CRL 2958 (CRL 2958Mλ) (Diffuse large cell lymphoma). FIG. 6E is a graph comparing the effect of monoclonal antibody mAb 4 versus an isotype-matched control antibody on inhibiting growth of mIgM-expressing B-cell line CRL 1596 (CRL 1596 Mλ) (Burkitt's lymphoma). FIG. 6F is a graph comparing the effect of monoclonal antibody mAb 4 versus an isotype-matched control antibody on inhibiting growth of mIgM-expressing B-cell line CRL 1432 (CRL 1432 Mλ) (Burkitt's lymphoma).

SUMMARY OF THE INVENTION

Figure 1A:
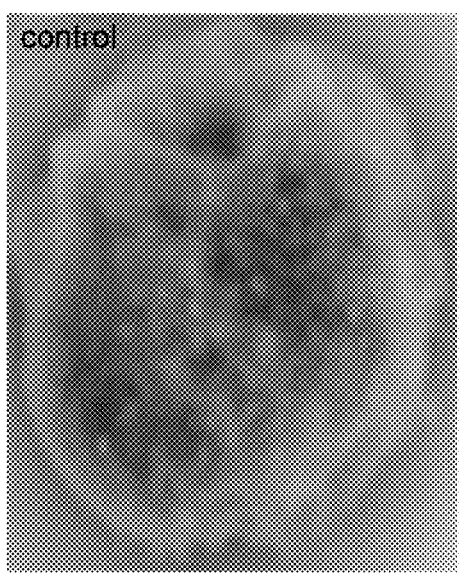
FIGS. 1A-1D. Cell line CRL 1648 Scanning Immuno-Electron microscopy (Burkitt's lymphoma).

The present invention relates to isolated antibodies specifically targeting membrane bound IgM (mIgM) of the B-cell Receptor Complex in B-cell lymphomas and leukemias. The antibodies of the invention may be a recombinant antibody. The antibodies of the invention may be monoclonal or a class-switched monoclonal derived from a monoclonal antibody of the invention, and a monoclonal antibody may be a mouse antibody, a human antibody, a chimeric antibody, or a humanized antibody.

Also included in the present invention are antigen binding regions (CDRs) derived from the light and/or heavy chain variable regions of said antibodies. The antibodies of the invention may be a recombinant antibody. The antibodies of the invention may be monoclonal, and a monoclonal antibody may be a human antibody, a chimeric antibody, or a humanized antibody.

The present invention includes an antibody that comprises a heavy chain variable region (VH) encoded by the nucleic acid sequence of SEQ ID NO: 1; and/or a light chain variable region (VL) encoded by the nucleic acid sequence of SEQ ID NO: 3.

The present invention includes an antibody that comprises a heavy chain variable region (VH) having the amino acid sequence depicted in SEQ ID NO: 2 and/or a light chain variable region (VL) having the amino acid sequence depicted in SEQ ID NO: 4.

The present invention includes an antibody that comprises a heavy chain variable region (VH) comprising a VH CDR1 having the amino acid sequence of SEQ ID NO: 5; a VH CDR2 having the amino acid sequence of SEQ ID NO: 6; and/or a VH CDR3 having the amino acid sequence of SEQ ID NO: 7; and/or a light chain variable region (VL) comprising a VL CDR1 having the amino acid sequence of SEQ ID NO: 8; a VL CDR2 having the amino acid sequence of SEQ ID NO: 9; and/or a VL CDR3 having the amino acid sequence of SEQ ID NO: 10.

The present invention includes an antibody that comprises a heavy chain variable region (VH) comprising a VH CDR1 having the amino acid sequence of SEQ ID NO: 5; a VH CDR2 having the amino acid sequence of SEQ ID NO: 6;

and a VH CDR3 having the amino acid sequence of SEQ ID NO: 7; and/or a light chain variable region (VL) comprising a VL CDR1 having the amino acid sequence of SEQ ID NO: 8; a VL CDR2 having the amino acid sequence of SEQ ID NO: 9; and a VL CDR3 having the amino acid sequence of SEQ ID NO: 10.

The present invention includes an antibody wherein the VH is encoded by a nucleotide sequence that hybridizes under stringent conditions to the complement of a nucleotide sequence that encodes the amino acid sequence of SEQ ID NO: 2; and/or a VL encoded by a nucleotide sequence that hybridizes under stringent conditions to the complement of a nucleotide sequence that encodes the amino acid sequence of SEQ ID NO: 4.

The present invention includes a VL sequence having at least 95% sequence identity to that set forth in SEQ ID NO: 4, and a VH sequence at least 95% sequence identity to that set forth in SEQ ID NO: 2.

The present invention includes human antigen-binding antibody fragments of the antibodies of the present invention including, but not limited to, Fab, Fab' and F(ab')$_2$, Fd, single-chain Fvs (scFv), single-chain antibodies, disulfide-linked Fvs (sdFv), diabodies, triabodies, or minibodies.

The present invention includes a monoclonal antibody designated mAb1-1 produced by a hybridoma cell line from fusion 117 (ATCC deposit number PTA-121719) and clones thereof.

The present invention includes a monoclonal antibody designated mAb2-2b produced by a hybridoma cell line from fusion 118 (ATCC deposit number PTA-121717) and clones thereof.

The present invention includes a monoclonal antibody designated mAb3-2b produced by a hybridoma cell line from fusion 118 (ATCC deposit number PTA-12718) and clones thereof.

The present invention includes a monoclonal antibody designated mAb4-2b produced by hybridoma cell line from fusion 119 (ATCC deposit number PTA-121716) and clones thereof.

The present invention relates to the antibody or antigen binding fragment of the present invention decreasing B-cell Receptor activity.

The present invention includes an antibody of the present invention further comprising a label.

The present invention includes the antibodies targeting the mIgM in the B-cell Receptor Complex in B-cell lymphomas and leukemias described above further comprising a cytotoxin, radioisotope or immunotoxin and their use in treating B-cell lymphomas and leukemias.

The present invention also includes antibodies that bind the same epitopes as antibody mAb4-2b.

The present invention also includes antibodies that bind the same epitope as antibody mAb1-1, mAb2-2b or mAb3-2b, including those antibodies that bind all isomeric forms of membrane proximal domain.

The present invention includes a composition comprising an antibody of the present invention and at least one of a physiologically acceptable carrier, diluent, excipient, or stabilizer.

The present invention relates to the use of an antibody or antigen binding fragment of the invention for the preparation of a medicament to treat B-cell lymphomas and leukemias in a subject.

The present invention relates to the use of the antibody or antigen binding fragment of the invention for the preparation of a medicament to decrease the activity of B-cell Receptor Complex.

The present invention includes a method of ameliorating or treating a B-cell lymphoma or leukemia in a patient, comprising administering to the patient an effective amount of an antibody that binds to B-cell mIgM and induces cell growth inhibition and/or apoptosis.

The present invention includes a composition comprising the antibodies according to the present invention in combination with a physiologically acceptable carrier, diluents, excipient, or stabilizer.

The present invention includes a method of killing or inhibiting the growth of B cells in a subject, comprising administering an effective amount of an antibody according to the present invention to a subject in need thereof, thereby killing or inhibiting the growth of the B cells in a subject.

The present invention includes a method of killing or inhibiting the growth of B cells in a subject, comprising administering an effective amount of the antibody of claim 1 to a subject in need thereof in combination with one or more anti-B-cell antibodies, a cytotoxin, and/or a radioisotope, thereby killing or inhibiting the growth of the B cells in a subject.

The present invention includes a hybridoma that produces an antibody of the present invention.

The present invention includes a hybridoma cell line designated ATCC PTA-121719 for producing the monoclonal antibody designated mAb1-1.

The present invention includes a hybridoma cell line designated ATCC PTA-121717 for producing the monoclonal antibody designated mAb2-2b.

The present invention includes a hybridoma cell line designated ATCC PTA-121718 for producing the monoclonal antibody designated mAb3-2b.

The present invention includes a hybridoma cell line designated ATCC PTA-121716 for producing the monoclonal antibody designated mAb4-2b.

The present invention relates to a complex comprising B-cell membrane IgM and any one of the antibody or antigen binding fragments described herein.

The present invention includes a method of producing an antibody comprising culturing a hybridoma cell line of the present invention under conditions suitable for the production of the antibody, and isolation of the antibody.

The present invention relates to an isolated nucleic acid encoding any of the antibodies or antigen binding fragments of the invention.

The present invention includes an isolated nucleic acid molecule encoding an antibody of the present invention wherein the nucleotide sequence comprises SEQ ID NO: 1 and/or 3.

The present invention includes an isolated nucleic acid molecule encoding an antibody of the present invention comprising the amino acid sequence of SEQ ID NO: 2 or 4.

The present invention includes an isolated nucleic acid molecule comprising a nucleic acid sequence that encodes a heavy chain variable region (VH) amino acid sequence set forth in SEQ ID NO: 2, and/or a light chain variable region (VL) amino acid sequence set forth in SEQ ID NO: 4.

The present invention relates to an expression vector comprising an isolated nucleic acid encoding any of the antibodies or antigen binding fragments of the invention. In one embodiment, the isolated nucleic acid encodes any of the VH or VL chains described herein. The invention also relates to a host cell comprising any of the expression vectors described herein.

The present invention relates to isolated polypeptides comprising the VH or VL domains or any of the antibodies or antigen binding fragments of the invention.

In certain embodiments, these nucleic acids, expression vectors or polypeptides of the invention are useful in methods of making an antibody.

The present invention includes a method for the detection of B-cell mIgM in a sample, comprising contacting the sample with an antibody of the present invention.

The present invention includes a method for the detection of B-cell mIgM in a patient sample, including determining minimal residual disease, comprising contacting the sample with an antibody of the present invention.

The present invention includes a method for the detection of B-cell mIgM micro-clustering thereby allowing for sub-typing B-cell malignancies and providing patient-specific prognostic information in a sample, comprising contacting the sample with an antibody of the present invention.

The present invention includes a method for purifying B-cell Receptors using an antibody of the present invention.

The present invention includes a kit comprising an antibody of the present invention in a predetermined amount in a container, and a buffer in a separate container.

The present invention includes a kit comprising a composition of the present invention described above in a predetermined amount in a container, and a buffer in a separate container.

DETAILED DESCRIPTION OF THE INVENTION

This invention is not limited to the particular methodology, protocols, cell lines, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells. Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

ABBREVIATIONS

Throughout the detailed description and examples of the invention the following abbreviations will be used:
ADCC Antibody-dependent cellular cytotoxicity
ATCC American Type Culture Collection
BCL2 or Bcl-2 B-cell lymphoma 2
BCR B-cell Receptor
BCRC B-cell Receptor Complex
BTK Tyrosine-protein kinase BTK
CDC Complement-dependent cytotoxicity
CDR Complementarity determining region in the immunoglobulin variable regions, defined using the Kabat numbering system
CHO Chinese hamster ovary
CLL Chronic lymphocytic leukemia
ELISA Enzyme-linked immunosorbant assay
FM Fluorescent microscopy
FR Antibody framework region: the immunoglobulin variable regions excluding the CDR regions
HRP Horseradish peroxidase
IFN Interferon
IC50 Concentration resulting in 50% inhibition
Ig Immunoglobulin
IgA Immunoglobulin A
IgD Immunoglobulin D
IgE Immunoglobulin D
IgG Immunoglobulin G
IgM Immunoglobulin M
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb, Mab, or MAb Monoclonal antibody
mAb 1 or mAb1 Monoclonal antibody mAb1-1
mAb 2 or mAb2 Monoclonal antibody mAb2-2b
mAb 3 or mAb3 Monoclonal antibody mAb3-2b
mAb 4 or mAb4 Monoclonal antibody mAb4-2b
mIg Cell-surface membrane bound immunoglobulin
mIgA Cell-surface membrane bound immunoglobulin A
mIgD Cell-surface membrane bound immunoglobulin D
mIgE Cell-surface membrane bound immunoglobulin D
mIgG Cell-surface membrane bound immunoglobulin G
mIgM Cell-surface membrane bound immunoglobulin M
PCR Polymerase chain reaction
PD Proximal domains
PI3K Phosphoinositide 3-kinase
PK Pharmacokinetics
SEM Scanning Immuno-Electron microscopy
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region
VL Immunoglobulin light chain variable region

Definitions

Terms used throughout this application are to be construed with ordinary and typical meaning to those of ordinary skill in the art. However, applicants desire that the following terms be given the particular definition as defined below.

The phrase "substantially identical" with respect to an antibody chain polypeptide sequence may be construed as an antibody chain exhibiting at least 70%, or 80%, or 90%, or 95% sequence identity to the reference polypeptide sequence. The term with respect to a nucleic acid sequence may be construed as a sequence of nucleotides exhibiting at least about 85%, or 90%, or 95%, or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody" is used in the broadest sense, including immunoglobulin molecules and immunologically active portions of immunoglobulin molecules, i.e., molecules that contain an antigen binding site that immunospecifically binds an antigen, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. Moreover, the term "antibody" (Ab) or "monoclonal antibody" (mAb) is meant to include both intact molecules, as well as antibody fragments (such as, for example, Fab and $F(ab')_2$ fragments) that are capable of specifically binding to a protein. Fab and $F(ab')_2$ fragments lack the Fc fragment of intact antibody, clear more rapidly from the circulation of the animal or plant, and may have less non-specific tissue binding than an intact antibody (Wahl, et al., J Nucl Med 24:316 (1983)).

As used herein, "anti-B-cell mIgM antibody" means an antibody which binds to human B-cell mIgM in such a manner so as to inhibit cell growth, internalize mIgM or induce apoptosis of the B-cells having this mIgM epitope.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs) also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The invention provides antibodies comprising modifications in these hybrid hypervariable positions. The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat, et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat, et al., unless otherwise indicated.

The term "antibody fragment" refers to a portion of a full-length antibody, generally the target binding or variable region. Examples of antibody fragments include Fab, Fab', $F(ab')_2$ and Fv fragments. The phrase "antigen binding fragment" of an antibody is a compound having qualitative biological activity in common with a full-length antibody. For example, an antigen binding fragment of an anti-B-cell mIgM antibody is one which can bind to a B-cell mIgM receptor in such a manner so as to prevent or substantially reduce the ability of such molecule from having the ability to bind to the B-cell mIgM. As used herein, "functional fragment" with respect to antibodies, refers to Fv, F(ab) and $F(ab')_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts and the naturally present class-switch variants containing identical CDR sequences. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well-known techniques. The parent monoclonal antibodies to be used in accordance with the present invention may be made by the hybridoma method first described by Kohler, et al., Nature 256:495 (1975), or may be made by recombinant methods. While monoclonal antibodies are usually produced in mice with identical genetic background as the fusion multiple myeloma partner (e.g., SP2/0), previously Yin et al., J Immunol Methods 144:165-173 (1991), have reported the use of non-identical partners in order to take advantage of genetically enhanced immune reactivity and affinity in different mouse strains.

The term "chimeric" antibody as used herein refers to an antibody having variable sequences derived from non-human immunoglobulins, such as rat or mouse antibody, and human immunoglobulins constant regions, typically chosen from a human immunoglobulin template. More recently, chimeric structures comprising the binding variable sequences of the monoclonal antibody and cell receptors have been developed. Chimeric shall also refer to antibodies having the humanized variable region sequences and mouse constant region sequences to allow for routine immunohistochemistry, flow cytometry or other assays optimized for murine reagents.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati, et al.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

"Transformation" of a cellular organism with DNA means introducing DNA into an organism so that the DNA is replicable, either as an extra chromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

"Mammal" for purposes of treatment refers to any animal classified as a mammal, including human, domestic and farm animals, nonhuman primates, and zoo, sports, or pet animals, such as dogs, horses, cats, cows, etc.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol, and silicones. In certain embodiments, depending on the context, the solid phase can comprise the well of an assay plate; in others it is a purification column (e.g., an affinity chromatography column).

The terms "activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., immunological activity/mg protein, concentration in a biological compartment, or the like. "Activity" may refer to modulation of components of the innate or the adaptive immune systems.

The term "proliferative activity" encompasses an activity that promotes, that is necessary for, or that is specifically associated with, e.g., normal cell division, as well as cancer, tumors, dysplasia, cell transformation, metastasis, and angiogenesis.

The terms "administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

The terms "treat" or "treating" means to administer a therapeutic agent, such as a composition containing any of the antibodies or antigen binding fragments of the present invention, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$ test, the U test according to Mann and Whitney, the Kruskal-Wallis test (H test), Jonckheere-Terpstra test and the Wilcoxon signed-rank test.

The term "treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agonist or antagonist to a human or animal subject, a cell, tissue, physiological compartment, or physiological fluid. "Treatment of a cell" also encompasses situations where the agonist or antagonist contacts the receptor, e.g., in the fluid phase or colloidal phase, but also situations where the agonist or antagonist does not contact the cell or the receptor.

Cell Lines

The following eleven human B-cell lineage cell lines and one murine cell line are referred to throughout the detailed description and examples of the invention as follows:

1. CRL 1432—Namalwa mIgM-L Burkitt's
2. CRL 1596—Ramos sIgM mIgM-L Burkitt's
3. CRL 1647—ST 486 sIgM mIgM-K Burkitt's
4. CRL 1648—CA 46 mIgM-K Burkitt's
5. CRL 1649—MC 116 mIgM-L Undifferentiated lymphoma
6. CRL 2260—HT mIgM-K Diffuse mixed B-cell lymphoma
7. CRL 2289—DB mIgG-L Large B-cell Lymphoma
8. CRL 2568—H2.8 murine IgG1-K Myeloma
9. CRL 2632—Diffuse large cell lymphoma IgGk
10. CRL 2958—SU-DHL-5 Diffuse large cell lymphoma mIgM
11. CRL 3006—JeKo-1-L mantle cell Lymphoma mIgM
12. SK007—Lymphoma mIgE These cell lines were obtained from the American Type Culture Collection (ATCC), 10801 University Boulevard, Manassas, Va. 20110, and tested for PD expression by RT-PCR. Cytoplasmic and secreted IgM fractions were confirmed by ELISA of supernatants and washed 0.01% NP-40 cell lysates.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, Cold spring Harbor Laboratory Press, 2nd ed. (1988)), which is hereby incorporated herein by reference in its entirety).

For example, an immunogen as described above may be administered to various host animals including, but not limited to, rabbits, mice, rats, etc., to induce the production of sera containing polyclonal antibodies specific for the antigen. The selection of the specific mouse strain for immunization may be critical for immunogens that elicit poor responses. Mouse strain tolerance may be overcome by pre-screening and selecting strains, such as testing those with autoimmune defects or more wild type immune reactivity. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, Multiple antigen peptide, and potentially useful human adjuvants such as BCG (Bacille Calmette-Guerin) and *Corynebacterium parvum*. Additional examples of adjuvants which may be employed include keyhole limpet hemocyanin with bound immunogen peptide, multiple antigen polypeptide with bound immunogen peptide, and the MPL-TDM adjuvant (monophosphoryl lipid A, synthetic trehalose dicorynomycolate). Immunization protocols are well known in the art and may be performed by any method that elicits an immune response in the animal host chosen. Adjuvants are also well known in the art.

Typically, the immunogen (with or without adjuvant) is injected into the mammal by multiple subcutaneous or intraperitoneal injections, or intramuscularly or through IV. The immunogen may include a target peptide, for membrane IgM: EGEVSADEEGFEN (SEQ ID NO: 11) or for membrane IgG: ELQLEESCAEAQDGELDG (SEQ ID NO: 12), purified B-cell mIgM, a fusion protein, or variants thereof. The target peptide for membrane IgM, EGEVSADEEGFEN (SEQ ID NO: 11), has 100% homology to a human IgM peptide hCG2038942 (Accession No. EAW81938.1) that has the sequence EGEVSEDEEGFE (SEQ ID NO: 13). Depending upon the nature of the peptides (i.e., percent hydrophobicity, percent hydrophilicity, stability, net charge, isoelectric point, multiple isomeric forms, etc.), it may be useful to conjugate the immunogen to a protein known to be immunogenic in the mammal being immunized. Such conjugation includes either chemical conjugation by active derivation of chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, multiple antigen peptide, ovalbumin, serum albumin, bovine thyroglobulin, soybean trypsin inhibitor, and promiscuous T helper peptides. Various adjuvants may be used to increase the immunological response as described above.

The antibodies of the present invention may comprise monoclonal antibodies. Monoclonal antibodies are antibodies which recognize a single antigenic site. Their uniform specificity makes monoclonal antibodies much more useful than polyclonal antibodies, which usually contain antibodies that recognize a variety of different antigenic sites. Monoclonal antibodies may be prepared using hybridoma technology, such as those described by Kohler, et al., Nature 256:495 (1975); U.S. Pat. No. 4,376,110; Harlow, et al. Antibodies: A Laboratory Manual, Cold Spring Harbor Laboratory Press, 2nd ed. (1988) and Hammerling, et al., Monoclonal Antibodies and T-Cell Hybridomas, Elsevier (1981), recombinant DNA methods, or other methods known to the artisan. Other examples of methods which may be employed for producing monoclonal antibodies include, but are not limited to, the human B-cell hybridoma technique (Kosbor, et al., Immunology Today 4:72 (1983); Cole, et al., Proc Natl Sci USA 80:2026 (1983)), and the EBV-hybridoma technique (Cole, et al., Monoclonal Antibodies and Cancer Therapy, pp. 77-96. Alan R. Liss (1985)). Such antibodies may be of any immunoglobulin class including IgG, IgM, IgE, and IgA, IgD and any subclass thereof. The hybridoma producing the mAb of this invention may be cultivated in vitro or in vivo.

In the hybridoma model, a host such as a mouse, a humanized mouse, a mouse with a human immune system, hamster, rabbit, camel, or any other appropriate host animal, is immunized to elicit lymphocytes that produce or are capable of producing antibodies that will specifically bind to the protein used for immunization. In the present invention, a mouse utilizing a human Ig genetic repertoire could not be used, as the initial B-cell itself would be a target of the desired antibody and would result in apoptosis of the B-cell. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high-level production of antibody by the selected antibody-producing cells, and are sensitive to a medium such as FIAT medium. Among these myeloma cell lines are murine myeloma lines, such as those derived from the MOPC-21 and MPC-11 mouse tumors and SP2/0 or X63-Ag8-653 cells available from the ATCC, 10801 University Boulevard, Manassas, Va., USA. Human myeloma and mouse-human heteromyeloma cell lines also have been described for the production of human monoclonal antibodies (Kozbor, J Immunol 133:3001 (1984); Brodeur, et al., Monoclonal Antibody Production Techniques and Applications, Marcel Dekker, Inc. pp. 51-63 (1987)). The mouse myeloma cell line NSO may also be used (European Collection of Cell Cultures, Salisbury, Wilshire, UK).

The culture medium in which hybridoma cells are grown is assayed for production of monoclonal antibodies directed against peptides, e.g., for IgM, EGEVSADEEGFEN (SEQ ID NO: 11) and for IgG, ELQLEESCAEAQDGELDG (SEQ ID NO: 12). The binding specificity of monoclonal antibodies produced by hybridoma cells may be determined by immunoprecipitation or by an in vitro binding assay, such as radioimmunoassay (RIA), immune blot, Westerns or enzyme-linked immunoabsorbent assay (ELISA). Such techniques are known in the art and within the skill of the artisan. The binding affinity of the monoclonal antibody can, for example, be determined by a Scatchard analysis (Munson, et al., Anal Biochem 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press, pp. 59-103 (1986)). Suitable culture media for this purpose include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones are suitably separated or isolated from the culture medium, ascites fluid, or serum by conventional immunoglobulin purification procedures such as, for example, protein A-Sepharose, hydroxylapatite chromatography, gel exclusion chromatography, gel electrophoresis, dialysis, or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. The hybridoma cells serve as a source of such DNA. Once isolated, the DNA may be placed into expression vectors, which are then transfected into host cells such as E. coli cells, NSO cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., Proc Natl Acad Sci USA 81:6851 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibody or the present invention or antigen binding fragment thereof that binds to membrane bound IgM (mIgM) of B-cell Receptor Complex (BCRC) can comprise one, two, three, four, five, or six of the complementarity determining regions (CDRs) of the antibodies disclosed herein. The one, two, three, four, five, or six CDRs may be independently selected from the CDR sequences of a single described antibody of the invention (e.g., Table 1, Table 2). In certain embodiments, one two or three CDRs are selected from the VL CDRs (e.g., Table 1; SEQ ID NOs:8-10) of the described antibody and/or one, two or three CDRs selected from the VH CDRs (e.g., Table 2; SEQ ID NOs: 5-7) of the described invention.

The isolated antibody of the present invention or antigen-binding fragment thereof that binds to mIgM of BCRC comprises an antibody light chain variable (VL) domain comprising one or more of CDR-L1, CDR-L2 or CDR-L3 of antibody mAb4-2b.

The isolated antibody of the present invention or antigen-binding fragment thereof that binds to mIgM of BCRC comprises an antibody heavy chain variable (VH) domain comprising one or more of CDR-H1, CDR-H2 or CDR-H3 of antibody mAb4-2b.

In a further embodiment the isolated antibody or antigen-binding fragment thereof that binds to mIgM of BCRC comprises an antibody light chain variable (VL) domain comprising one or more of CDR-L1, CDR-L2 or CDR-L3 of antibody mAb4-2b, and an antibody heavy chain variable (VH) domain comprising one or more of CDR-H1, CDR-H2 or CDR-H3 of antibody mAb4-2b. Sequences of light and heavy chain CDRs of the mAb4-2b antibody of the present invention are provided in Tables 1 and 2, respectively.

TABLE 1

Light Chain CDRs

| Antibody | CDR1 | CDR2 | CDR3 |
|---|---|---|---|
| mAb4-2b | SEQ ID NO: 8 | SEQ ID NO: 9 | SEQ ID NO: 10 |

TABLE 2

Heavy Chain CDRs

| Antibody | CDR1 | CDR2 | CDR3 |
|---|---|---|---|
| mAb4-2b | SEQ ID NO: 5 | SEQ ID NO: 6 | SEQ ID NO: 7 |

The invention also provides isolated polypeptides comprising the VL domains (e.g., SEQ ID NO: 4) and isolated polypeptides comprising the VH domains (e.g., SEQ ID NO: 2) of the antibodies of the invention. In other embodiments the invention provides antibodies or antigen binding fragment thereof that specifically binds to mIgM of BCRC and has VL domains and VH domains with at least 50%, 75%, 80%, 85%, 90%, 95%, 98% or 99% sequence identity with SEQ ID NOs: 2 and 4 while still exhibiting the desired binding and functional properties. In another embodiment, the antibody or antigen binding fragment of the present invention comprises VL and VH domains (with and without signal sequence) having up to 0, 1, 2, 3, 4, 5, 6, 7, 8, 9, 10 or more conservative or non-conservative amino acid substitutions, while still exhibiting the desired binding and functional properties.

"Conservatively modified variants" or "conservative substitution" refers to substitutions of amino acids in a protein with other amino acids having similar characteristics (e.g., charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity. Various embodiments of the antibody or antigen binding fragment of the present invention comprise polypeptide chains with the sequences disclosed herein, e.g., SEQ ID NOs: 2, 4, 5, 6, 7, 8, 9, and 10, or polypeptide chains comprising up to 1, 2, 3, 4, 5, 6, 7, 8, 9, 10, 12, 15, 20 or more conservative amino acid substitutions. Exemplary conservative substitutions are set forth in Table 3.

TABLE 3

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such as antigen affinity and/or specificity. Such variants include, but are not limited to, replacement of an amino acid with one having similar properties, such as the conservative amino acid substitutions of Table 3.

In another embodiment, the invention provides an antibody or antigen binding fragment thereof that specifically binds human mIgM of BCRC and has VL domains or VH domains with at least 95%, 90%, 85%, 80%, 75% or 50% sequence homology to one or more of the VL domains or VH domains described herein, and exhibits specific binding to human mIgM of BCRC. In another embodiment, the binding antibody or antigen binding fragment thereof of the present invention comprises VL and VH domains (with and without signal sequence) having up to 1, 2, 3, 4, or 5 or more amino acid substitutions, and exhibits specific binding to human mIgM of BCRC.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, these fragments were derived via proteolytic digestion of intact antibodies (see, e.g., Morimoto, et al., J Biochem Biophys Methods 24:107 (1992); Brennan, et al., Science 229:81 (1985)). For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. However, these fragments can now be produced directly by recombinant host cells. For example, the antibody fragments can be isolated from an antibody phage library. Alternatively, F(ab')$_2$-SH fragments can be directly recovered from *E. coli* and chemically coupled to form F(ab'), fragments (Carter, et al., Bio/Technology 10:163 (1992). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (Fv) (PCT Publication No. WO 93/16185).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi, et al., BioTechniques 4:214 (1986); Gillies, et al., J Immunol Methods 125:191 (1989); U.S. Pat. Nos. 5,807,715; 4,816,567; and 4,816,397, which are incorporated herein by reference in their entirety.

A humanized antibody is designed to have greater homology to a human immunoglobulin than animal-derived monoclonal antibodies. Humanization is a technique for making a chimeric antibody wherein substantially less than an intact human variable domain has been substituted by the corresponding sequence from a non-human species. Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. No. 5,585,089; Riechmann, et al., Nature 332:323 (1988), which are incorporated herein by reference in their entireties. Antibodies can be humanized using a variety of techniques known in the art including, for example, CDR-grafting (European App. No. EP 239,400; PCT Publication No. WO 91/09967; U.S. Pat. Nos. 5,225,539; 5,530,101; and 5,585,089), veneering or resurfacing (European App. No. EP 592,106; European App. No. EP 519,596; Padlan, Molecular Immunology 28:489 (1991); Studnicka, et al., Protein Engineering 7:805 (1994); Roguska, et al., Proc Natl Acad Sci USA 91:969 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones, et al., Nature 321:522 (1986); Riechmann, et al., Nature 332:323 (1988); Verhoeyen, et al., Science 239:1534 (1988)), by substituting non-human CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and some possible FR residues are substituted from analogous sites in rodent antibodies.

It is further important that humanized antibodies retain higher affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is maximized, although it is the CDR residues that directly and most substantially influence antigen binding.

The choice of human variable domains, both light and heavy, to be used in making the humanized antibodies is important to reduce antigenicity. According to the so-called "best-fit" method, the sequence of the variable domain of a non-human antibody is screened against the entire library of known human variable-domain sequences. The human sequence which is closest to that of that of the non-human parent antibody is then accepted as the human FR for the humanized antibody (Sims, et al., J Immunol 151:2296 (1993); Chothia, et al., J Mol Biol 196:901 (1987)).

Another method uses a particular framework derived from the consensus sequence of all human antibodies of a particular subgroup of light or heavy chains. The same framework may be used for several different humanized antibodies (Carter, et al., Proc Natl Acad Sci USA 89:4285 (1992); Presta, et al., J Immunol 151:2623 (1993)). An antibody of the invention can comprise any suitable human or human consensus light or heavy chain framework sequences, provided that the antibody exhibits the desired biological characteristics (e.g., a desired binding affinity). In some embodiments, one or more (such as 2, 3, 4, 5, 6, 7, 8, 9, or more) additional modifications are present within the human and/or human consensus non-hypervariable region sequences. In one embodiment, an antibody of the invention comprises at least a portion (or all) of the framework sequence of human light chain. In one embodiment, an antibody of the invention comprises at least a portion (or all) of the framework sequence of human heavy chain. In one embodiment, an antibody of the invention comprises at least a portion (or all) of human subgroup I framework consensus sequence. In some embodiments, antibodies of the invention comprise a human subgroup III heavy chain framework consensus sequence. In one embodiment, the framework consensus sequence of the antibody of the invention comprises substitution at position 71, 73 and/or 78. In some embodiments of these antibodies, position 71 is A, 73 is T and/or 78 is A.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT Publication Nos. WO 98/46645, WO 98/50433, WO 98/24893, WO 98/16654, WO 96/34096, WO 96/33735, and WO 91/10741; each of which is incorporated herein by reference in its entirety. The techniques of Cole, et al. and Boerner, et al. are also available for the preparation of human monoclonal antibodies (Cole, et al., Monoclonal Antibodies and Cancer Therapy, Alan R. Riss (1985); and Boerner, et al., J Immunol 147:86 (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. See, e.g., Jakobovitis, et al., Proc Acad Sci USA 90:2551 (1993); Jakobovitis, et al., Nature 362:255 (1993); Bruggermann, et al., Year in Immunol 7:33 (1993); Duchosal, et al., Nature 355:258 (1992)).

The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg, et al., Int Rev Immunol 13:65-93 (1995). For a detailed discussion of this technology for producing human antibodies and human monoclonal antibodies and protocols for producing such antibodies, see, e.g. PCT Publication Nos. WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Human mAbs could also be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach, a selected non-human monoclonal antibody, e.g., a mouse antibody, is used to guide the selection of a completely human antibody recognizing the same epitope (Jespers, et al., Bio/Technology 12:899 (1988)). Of note, human B-cells cannot be used to generate the specific monoclonal antibodies required, as the monoclonal antibodies would be self-reactive with the primary immunized B-cell initiating the response.

Further, antibodies to the polypeptides of the invention can, in turn, be utilized to generate anti-idiotype antibodies that "mimic" polypeptides of the invention using techniques well known to those skilled in the art (See, e.g., Greenspan, et al., FASEB J 7:437 (1989); Nissinoff, J Immunol 147:2429 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards B-cell mIgM, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein, et al., Nature 305:537

(1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in PCT Publication No. WO 93/08829 and in Traunecker, et al., EMBO J 10:3655 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh, et al., Meth In Enzym 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, one can generate single-domain antibodies to B-cell mIgM. Examples of this technology have been described in PCT Publication No. WO9425591 for antibodies derived from Camelidae heavy chain Ig, as well in US Publication No. 20030130496 describing the isolation of single domain fully human antibodies from phage libraries.

One can also create a single peptide chain binding molecules in which the heavy and light chain Fv regions are connected. Single chain antibodies ("scFv") and the method of their construction are described in U.S. Pat. No. 4,946,778. Alternatively, Fab can be constructed and expressed by similar means. All of the wholly and partially human antibodies are less immunogenic than wholly murine mAbs, and the fragments and single chain antibodies are also less immunogenic.

Antibodies or antibody fragments can be isolated from antibody phage libraries generated using the techniques described in McCafferty, et al., Nature 348:552 (1990); Clarkson, et al., Nature 352:624 (1991) and Marks, et al., J Biol 222:581 (1991), which describe the isolation of murine and human antibodies, respectively, using phage libraries. Subsequent publications describe the production of high affinity (nM range) human antibodies by chain shuffling (Marks, et al., Bio/Technology 10:779 (1992)), as well as combinatorial infection and in vivo recombination as a strategy for constructing very large phage libraries (Waterhouse, et al., Nuc Acids Res 21:2265 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc Natl Acad Sci USA 81:6851 (1984)).

Another alternative is to use electrical fusion rather than chemical fusion to form hybridomas. This technique is well established. Instead of fusion, one can also transform a B cell to make it immortal using, for example, an Epstein Barr Virus, or a transforming gene. See, e.g., "Continuously Proliferating Human Cell Lines Synthesizing Antibody of Predetermined Specificity," Zurawaki, et al., in Monoclonal Antibodies, ed. by Kennett, et al., Plenum Press, pp. 19-33. (1980)). Anti-B-cell mIgM mAbs can be raised by immunizing rodents (e.g., mice, rats, hamsters, and guinea pigs) with B-cell mIgM protein, fusion protein, or its fragments expressed by either eukaryotic or prokaryotic systems. Other animals can be used for immunization, e.g., non-human primates, transgenic mice expression immunoglobulins, and severe combined immunodeficient (SCID) mice transplanted with human B lymphocytes. Hybridomas can be generated by conventional procedures by fusing B lymphocytes from the immunized animals with myeloma cells (e.g., Sp2/0 and NSO), as described earlier (Kohler, et al., Nature 256:495 (1975)). In addition, anti-B-cell mIgM antibodies can be generated by screening of recombinant single-chain Fv or Fab libraries from human B lymphocytes in phage-display systems. The specificity of the mAbs to B-cell mIgM can be tested by ELISA, Western immunoblotting, or other immunochemical techniques. The inhibitory activity of the antibodies on CD4+ T cell activation can be assessed by proliferation, cytokine release, and apoptosis assays. The hybridomas in the positive wells are cloned by limiting dilution. The antibodies are purified for characterization for specificity to human B-cell mIgM by the assays described above.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences are described in the Sequence Listing (e.g., SEQ ID NOs: 1 and 3). The invention also encompasses polynucleotides that hybridize under stringent or lower stringency hybridization conditions to polynucleotides that encode an antibody of the present invention.

Preferably, the nucleic acids hybridize under low, moderate or high stringency conditions, and encode antibodies that maintain the ability to specifically bind to mIgM of BCRC. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., Molecular Cloning, A Laboratory Manual, Cold Spring Harbor Laboratory, $2^{nd}$ ed. (1990), $3^{rd}$ ed. (2001)). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., Molecular Cloning, A Laboratory Manual, 9.50-9.51, Cold Spring Harbor Laboratory, $2^{nd}$ ed. (1990), $3^{rd}$ ed. (2001)). For hybridization with shorter nucleic acids, e.g., oligonucleotides, the position of mismatches becomes more important, and the length of the oligonucleotide determines its specificity (see Sambrook, et al., Molecular Cloning, A Laboratory Manual, 11.7-11.8, Cold Spring Harbor Laboratory, $2^{nd}$ ed. (1990), $3^{rd}$ ed. (2001)).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier, et al., Bio/Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook, et al., Molecular Cloning, A Laboratory Manual, Cold Spring Harbor Laboratory $2^{nd}$ ed. (1990), $3^{rd}$ ed. (2001); Ausubel, et al., eds., Current Protocols in Molecular Biology, John Wiley & Sons (1998), which are both incorporated by reference herein in their entireties), to generate antibodies having a different amino acid sequence, for example, to create amino acid substitutions, deletions, and/or insertions.

In a specific embodiment, the amino acid sequence of the heavy and/or light chain variable domains may be inspected to identify the sequences of the CDRs by well-known methods, e.g. by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia, et al., J Mol Biol 278: 457 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison, et al., Proc Natl Acad Sci 81:851 (1984); Neuberger, et al., Nature 312:604 (1984); Takeda, et al., Nature 314:452 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423 (1988); Huston, et al., Proc Natl Acad Sci USA 85:5879 (1988); and Ward, et al., Nature 334:544 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra, et al., Science 242:1038 (1988)).

Vectors and Host Cells

In another aspect, the present invention provides isolated nucleic acid sequences encoding an antibody as disclosed herein, vector constructs comprising a nucleotide sequence encoding the antibodies of the present invention, host cells comprising such a vector, and recombinant techniques for the production of the antibody.

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Standard techniques for cloning and transformation may be used in the preparation of cell lines expressing the antibodies of the present invention.

Vectors

Many vectors are available. The vector components generally include, but are not limited to, one or more of the following: a signal sequence, an origin of replication, one or more marker genes, an enhancer element, a promoter, and a transcription termination sequence. Recombinant expression vectors containing a nucleotide sequence encoding the antibodies of the present invention can be prepared using well known techniques. Expression vectors may include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence. An example of a useful expression vector for expressing the antibodies of the present invention may be found in PCT Publication No. WO 04/070011, which is incorporated herein by reference.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435; 5,698,417; and 6,204,023.

Host Cells

Host cells useful in the present invention are prokaryotic, yeast, or higher eukaryotic cells and include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces*, *Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in the present invention include gram negative or gram positive organisms such as *E. coli*, *B. subtilis*, *Enterobacter*, *Erwinia*, *Klebsiella*, *Proteus*, *Salmonella*, *Serratia*, and *Shigella*, as well as Bacilli, *Pseudomonas*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 (Pharmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, J Mol Biol 219:37 (1991); Schoepfer, Gene 124:83 (1993)). Promoter sequences commonly used for recombinant prokaryotic host cell expression vectors include T7, (Rosenberg, et al., Gene 56:125 (1987)); β-lactamase (penicillinase), lactose promoter system (Chang, et al., Nature 275:615 (1978), Goeddel, et al., Nature 281:544 (1979)); tryptophan (trp) promoter system (Goeddel, et al., Nucl Acids Res 8:4057 (1980)); and tac promoter (Sambrook, et al., Molecular Cloning, A Laboratory Manual, 2nd ed., Cold Spring Harbor Laboratory (1990)).

Yeasts or filamentous fungi useful in the present invention include those from the genus *Saccharomyces*, *Pichia*, *Actinomycetes*, *Kluyveromyces*, *Schizosaccharomyces*, *Candida*, *Trichoderma*, *Neurospora*, and filamentous fungi such as *Neurospora*, *Penicillium*, *Tolypocladium*, and *Aspergillus*. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman, et al., J Biol Chem 255:2073 (1980)) or other glycolytic enzymes (Holland, et al., Biochem 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer, et al., Gene 107:285 (1991). Other suitable promoters and vectors for yeast and yeast transformation protocols are well known in the art. Yeast transformation protocols are well known. One such protocol is described by Hinnen, et al., Proc Natl Acad Sci 75:1929 (1978). The Hinnen protocol selects for Trp transformants in a selective medium.

Mammalian or insect host cell culture systems may also be employed to express recombinant antibodies. In principle, any higher eukaryotic cell culture is workable, whether from vertebrate or invertebrate culture. Examples of invertebrate cells include plant and insect cells (Luckow, et al., Bio/Technology 6:47 (1988); Miller, et al., Genetics Engineering, Setlow, et al., eds. Vol. 8, pp. 277-9, Plenam Publishing (1986); Mseda, et al., Nature 315:592 (1985)). For example, Baculovirus systems may be used for production of heterologous proteins. In an insect system, *Autographa californica* nuclear polyhedrosis virus (AcNPV) may be used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter). Other hosts that have been identified include *Aedes, Drosophila melanogaster*, and *Bombyx mori*. A variety of viral strains for transfection are publicly available, e.g., the L-1 variant of AcNPV and the Bm-5 strain of *Bombyx mori* NPV, and such viruses may be used as the virus herein according to the present invention, particularly for transfection of *Spodoptera frugiperda* cells. Moreover, plant cell cultures of cotton, corn, potato, soybean, *petunia*, tomato, and tobacco can also be utilized as hosts.

Vertebrate cells, and propagation of vertebrate cells, in culture (tissue culture) has become a routine procedure. See Tissue Culture, Kruse, et al., eds., Academic Press (1973). Examples of useful mammalian host cell lines are monkey kidney; human embryonic kidney line; baby hamster kidney cells; Chinese hamster ovary cells/-DHFR (CHO, Urlaub, et al., Proc Acad Sci USA 77:4216 (1980)); mouse sertoli cells; human cervical carcinoma cells (HELA); canine kidney cells; human lung cells; human liver cells; mouse mammary tumor; and NSO cells.

Host cells are transformed with the above-described vectors for antibody production and cultured in conventional nutrient media modified as appropriate for inducing promoters, transcriptional and translational control sequences, selecting transformants, or amplifying the genes encoding the desired sequences. Commonly used promoter sequences and enhancer sequences are derived from polyoma virus, Adenovirus 2, Simian virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

The host cells used to produce the antibodies of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham, et al., Meth Enzymol 58:44 (1979), Barnes, et al., Anal Biochem 102:255 (1980), and U.S. Pat. No. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Also included in the present invention are polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences. Polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm wherein the parameters of the algorithm are selected to give the largest match between the respective sequences over the entire length of the respective reference sequences, are also included in the present invention.

Sequence identity refers to the degree to which the amino acids of two polypeptides are the same at equivalent positions when the two sequences are optimally aligned. Sequence similarity includes identical residues and non-identical, biochemically related amino acids. Biochemically related amino acids that share similar properties and may be interchangeable are discussed above.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

In another embodiment, the invention relates to an isolated nucleic acid or nucleic acids, for example DNA, encoding the polypeptide chains of the isolated antibodies or antigen binding fragments of the invention. In one embodiment, the isolated nucleic acid encodes an antibody or antigen binding fragment thereof comprising at least one mature antibody light chain variable (VL) domain and at least one mature antibody heavy chain variable (VH) domain, wherein the VL domain comprises at least three CDRs having the sequence of SEQ ID NO: 3, and the VH domain comprises at least three CDRs having the sequence of SEQ ID NO: 1. In some embodiments, the isolated nucleic acid encodes both a light chain and a heavy chain on a single nucleic acid molecule, and in other embodiments, the light and heavy chains are encoded on separate nucleic acid molecules. In another embodiment, the nucleic acids further encode a signal sequence.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative, or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as *E. coli*, and eukaryotic cells are commonly used for the expression of a recombinant antibody molecule, especially for the expression of whole recombinant antibody molecule. For example, mammalian cells such as CHO, in conjunction with a vector such as the major intermediate early gene promoter element from human cytomegalovirus, are an effective expression system for antibodies (Foecking, et al., Gene 45:101 (1986); Cockett, et al., Bio/Technology 8:2 (1990)).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for one to two days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler, et al., Cell 11:223 (1977)), hypoxanthine-guanine phosphoribosyltransferase (Szybalska, et al., Proc Nail Acad Sci USA 48:202 (1992)), and adenine phosphoribosyltransferase (Lowy, et al., Cell 22:817 (1980)) genes, which can be employed in tk, hgprt or aprt-cells, respectively. Also, anti-metabolite resistance can be used as the basis of selection for the following genes: dhfr, which confers resistance to methotrexate (Wigler, et al., Proc Natl Acad Sci USA 77:357 (1980); O'Hare, et al., Proc Natl Acad Sci USA 78:1527 (1981)); gpt, which confers resistance to mycophenolic acid (Mulligan, et al., Proc Natl Acad Sci USA 78:2072 (1981)); neo, which confers resistance to the aminoglycoside G-418 (Wu, et al., Biotherapy 3:87 (1991)); and hygro, which confers resistance to hygromycin (Santerre, et al., Gene 30:147 (1984)). Methods commonly known in the art of recombinant DNA technology may be routinely applied to select the desired recombinant clone, and such methods are described, for example, in Ausubel, et al., eds., Current Protocols in Molecular Biology, John Wiley & Sons (1993); Kriegler, Gene Transfer and Expression, A Laboratory Manual, Stockton Press (1990); and in Chapters 12 and 13, Dracopoli, et al., eds, Current Protocols in Human Genetics, John Wiley & Sons (1994); Colberre-Garapin, et al., J Mol Biol 150:1 (1981), which are incorporated by reference herein in their entireties.

The expression levels of an antibody molecule can be increased by vector amplification (for a review, see Bebbington, et al., "The use of vectors based on gene amplification for the expression of cloned genes in mammalian cells," DNA Cloning, Vol. 3. Academic Press (1987)). When a marker in the vector system expressing antibody is amplifiable, increase in the level of inhibitor present in the culture of host cell will increase the number of copies of the marker gene. Since the amplified region is associated with the antibody gene, production of the antibody will also increase (Crouse, et al., Mol Cell Biol 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc Natl Acad Sci USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See, e.g., PCT Publication No. WO 93/21232; European App. No. EP 439,095; Naramura, et al., Immunol Lett 39:91 (1994); U.S. Pat. No. 5,474,981; Gillies, et al., Proc Nail Acad Sci USA 89:1428 (1992); Fell, et al., J Immunol 146:2446 (1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide (SEQ ID NO: 18), such as the tag provided in a pQE vector (QIAGEN, Inc., 9259 Eton Avenue, Chatsworth, Calif., 91311), among others, many of which are commercially available. As described in Gentz, et al., Proc Natl Acad Sci USA 86:821 (1989), for instance, hexa-histidine (SEQ ID NO: 18) provides for convenient purification of the fusion protein. Other peptide tags useful for purification include, but are not limited to, the "HA" tag, which corresponds to an epitope derived from the influenza hemagglutinin protein (Wilson, et al., Cell 37:767 (1984)) and the "flag" tag.

Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, may be removed, for example, by centrifugation or ultrafiltration. Carter, et al., Bio/Technology 10:163 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human IgG1, IgG2 or IgG4 heavy chains (Lindmark, et al., J Immunol Meth 62:1 (1983)). Protein G is recommended for all mouse isotypes and for human IgG3 (Guss, et al., EMBO J5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Antibodies to mIgM of B-Cell Receptor Complex

The present invention relates to antibodies specifically targeting the membrane bound IgM (mIgM) component of the B-cell Receptor Complex (BCRC). As the majority of B-cell lymphomas and leukemias express mIgM on their cell surface, these antibodies can be used in the study of this molecule and the diagnosis and treatment of mIgM associated diseases.

The B-cell Receptor Complex is the central signaling element of the B-cell arm of the immune system controlling differentiation, cell growth and apoptosis. This cell surface molecular complex is expressed and constitutively activated in all B-cell malignancies (Tsubata T, et al., B cell signaling. Introduction. 20:675-678 (2000); Gauld S B, et al., Science 296:1641-1642 (2002); Girurajan M, et al., J Immunol 15:5715-5719 (2006)). The BCRC consists of a trans-membrane version of the secreted form of Ig (the receptor), closely associated with CD79αβ (the signaling element) (See, Reth M, Nature 338:383-384 (1989); Gold M R. et al., Proc Natl Acad Sci USA 88:3436-3440 (1991); Jugloff L S. et al., J Immunol 159:1139-1146 (1991); Cambier J C, et al., FASEB J 6:3207-3217 (1992); Flaswinkel H, et al., EMBO J 13:83-89 (1994); Burkhardt A L, et al., Mol Cell Biol 14:1095-1103 (1994); Rowley R B, et al., J Biol Chem 270:11590-11594 (1995); Kabak S, et al., Biochem Biophys Res Commun 324:1249-1255 (2004); Patterson H C, et al., Immunity 25:55-65 (2006); Polson A G, et al., Blood 110: 616-623 (2007)). A small extracellular peptide segment (extracellular proximal domain, ECPD or PD) is also present between the trans-membrane sequence of the mIg and the homologous Ig consensus sequence present in both the membrane and secreted form of the Ig (Bestagno M, et al., Biochemistry 40:10686-10692 (2001); Poggianella M, et al., J Immunol 177:3597-3605 (2006)). This PD is unique for each membrane Ig class and it is not present on the corresponding secreted Ig form. In addition, based on a search of the human genome database, the PD sequence for each Ig membrane class is unique with respect to all sequences contained therein and compared to the reported corresponding murine sequences. Thus, a genome data bank search of the specific sequence for each of the class-specific PDs yielded only its corresponding membrane Ig class. No other membrane proteins could be identified that use these sequences as determined by the gene bank searches. In addition, no homologous peptide sequences were found to suggest the evolutionary derivation of these small domains.

Because of the presence of large amounts of Ig in circulating blood, the homologue membrane bound Ig (mIg) was not thought to be a relevant target for drug development. The present application shows that the BCRC can be targeted without interference from circulating Ig by targeting the short peptide linkers that present extracellularly between the trans-membrane hydrophobic amino acid sequence and the consensus secreted Ig homologue sequence, i.e., PD. In addition, mRNA splice variants comprising the mIgM constant domain 4 (µC4) provide new important specific epitopes. These findings led to the generation herein of anti-PD mAbs, i.e., anti-mIgM and anti-mIgG PD mAbs and an antibody binding a unique µC4 epitope. These mAbs target mIgM or mIgG class-specific BCRCs and thereby can be used to purify these Ig receptors, and to further explore and discover other neo-antigens present in the mIg compared to the corresponding serum version. Because of their unique sequences, it is hypothesized that anti-PD mAbs could modulate downstream signaling pathways in the signal-transduction from mIg to CD79αβ if the signal is mediated through PDs. An advantage of this targeting approach of utilizing anti-PD mAbs is that disruption of downstream pathways associated with BCRC would be expected to be modulated only in B-cells and restricted to the targeted Ig class, e.g., mIgM expressing cells only. In addition to the specific epitopes contained in the PD, the adjacent or proximal sequence contained within the constant region 4 of IgM, µC4, is truncated in the mIgM compared to the sIgM by deletion of the 20 proximal amino-acids of this domain. Thus, one would expect to detect additional immunologically defined neo-epitopes further distinguishing mIgM from sIgM in mIgM constant region 4, µC4. The truncation is also responsible for loss of a glycosylation site; the J-Chain binding is absent and this region is proximal to the mIg clustering site localized in the µC4 domain (See, Tolar P et al, Immunity 30(1):44-55 (2009)). It became clear that mAbs could be generated to neo-epitopes in mIgM constant domain 4 and one such mAb was isolated that also modulates signaling through the BCRC. As mIgM is the receptor component of the BCRC, it must transmit the activation signal to CD79αβ where the intra-cellular phospho-kinases reside. The exact point of signal transmission from one molecule to the other is still not known.

With a goal to specifically modulate the BCRC, specific monoclonal antibodies (mAbs) targeting the mIg molecule at its PD, anti-PD mAbs, were generated. A large panel of peptide-specific mAbs detecting the 13-mer peptide PD sequence (EGEVSADEEGFEN) (SEQ ID NO: 11) specific for the mIgM molecule and the 18-mer peptide PD sequence (ELQLEESCAEAQDGELDG) (SEQ ID NO: 12) specific for mIgG were generated and found to have peptide specific binding and cell binding for peptide expressing cells. High affinity anti-PD monoclonal antibodies (mAbs) were generated by immunization techniques described below. These monoclonal antibodies were shown by ELISA, Western blots and Scanning Immuno-Electron Microscopy (SEM) to bind to mIgM protein and mIgM+ expressing cell lines CA 46 (CRL 1648), SU-DHL-5 (CRL 2958), Ramos (CRL-1596), Namalwa (CRL-1432), ST 486 (CRL-1647), MC 116 (CRL-1649), and HT (CRL-2260). Using these high affinity anti-PD monoclonal antibodies, mIgM was immune-affinity purified and used to immunize mice. Second generation antibodies detecting conformational epitopes on BCRC and not reacting with sIgM in ELISA/Western/SEM assays were collected. Growth inhibition was assessed by MTT/CAS-PASE and clonogenic limiting dilution assays as described below. Four monoclonal antibodies designated mAb1-1, mAb2-2b, mAb3-2b and mAb4-2b were selected for further studies.

In the course of generating and assessing these specific mAbs to mIgM PD/purified mIgM, several issues and challenges arose:

1. Initial clones collected were of low affinity despite the unique sequence of the antigen target. Screening immunized Balb/c mice demonstrated that the sera responses were poor. Various adjuvants were investigated without achieving measurable increased titer or affinity of the sera samples. Various strains of mice were subsequently tested and only CD-1 mice were found to be appropriate hosts for generating high affinity antibodies.

2. The target polypeptide exists in at least three isomeric forms. To generate clinically appropriate mAb reagents, mAbs were screened for those mAbs that recognized all isomeric forms of the target PD.

3. In an effort to enhance the affinity of the murine antibody immune response, and to broaden the search for additional epitopes, purified mIgM preparations from cell extracts (acquired from a mAb1-1 immuno-affinity column) were incorporated into the immunogen (by co-administration with mIgM PD-peptide-MAP immunogen).

4. Antibody mAb1 was derived from a fusion comprising a mIgM-PD peptide-MAP immunogen only, whereas all other antibodies (mAb 2, mAb 3 and mAb 4) were generated using the purified mIgM in addition to a mIgM PD-peptide-MAP immunogen. To indicate that these mAbs were derived from fusions using different immunogens, the suffix 1 was added to mAb1 (mAb1-1) and the suffix 2 was added to the other antibodies (mAb2-2, mAb3-2 and mAb2-4). Additionally, since the purified mIgM used to generate the antibodies mAb2, mAb3 and mAb4 was derived from cell line b (CA 46, CRL 1648) extract, the letter b was added to the suffix 2 (mAb2-2b, mAb3-2b and mAb4-2b).

5. During the immunizations with purified mIgM, mAbs were generated to an epitope shared with the 4th constant region of mIgM that was not detected on serum IgM. This is a consequence of neo-antigens generated due to the terminal deletion of the distal 20 amino acids in the membrane IgM as compared to serum IgM mRNA splice variants. mAb4-2b proves that structure changes in the 4th constant region of mIgM induced unique conformation epitopes in the IgM domain µC4.

The following studies, which were required to prove mAb specificity and to investigate critical aspects of the biologic activity, are presented later in the application in the following order:

1. Generation of and selection of hybridoma panels
2. Specificity studies on live target cells and cell extracts (Table 4)
3. Specificity studies for target peptide, isomers and cell extracts (Tables 5, 6)
4. Molecular specificity studies of inhibition of direct binding to immune-affinity mIgM or Perfect-FOCUS™ extract (Tables 7, 8).
5. Molecular epitope mapping by competitive mAb binding and 6-mer inhibition (Tables 9, 10)
6. Scanning Electron Microscopy binding studies (Tables 11-18, FIGS. 1-5)
7. mAb binding mediated BCRC internalization (Tables 19, FIG. 2)
8. mAb4-2b mediated growth inhibition, anti-clonogenic activity and apoptosis (Tables 20-24 and FIGS. 6-7)

As shown later in the present application, cell surface binding assays demonstrated the specificity of these monoclonal antibodies by testing against a panel of mIgM+vs mIgM−(mIgG+) live cells/fixed cells or extracts. In addition, normal or Waldenstrom's Macroglobulinemia sera failed to block or reduce mAb binding to mIgM+ cells, results which were also confirmed by SEM. These two studies clearly demonstrate achievement of the ability to target B-cells specifically, in vivo.

At 37° C., anti-PD monoclonal antibodies (mAb1-1, mAb2-2b, mAb3-2b) internalized mIgM (BCRC) by 30 mins, but they did not modulate cell growth inhibition. Second generation mAb4-2b also mediated mIgM (BCRC) internalization, but additionally, in low density cultures, cell growth inhibition, anti-clonogenic activity and apoptosis were observed. Apoptosis was seen in a variety of malignant B-cell lines including high and low mIgM/CD79αβ expressing cells.

No antibodies have been reported that (1) bind mIgM expressing cells specifically and (2) do not react with human serum IgM, and have high enough avidity to immune-affinity purify mIgM. Commercial preparations of mIgM are of low quality. The present invention provides such antibodies capable of mIgM purification despite the presence of serum or secreted IgM in the cytoplasm of these B-cells.

The data presented below demonstrate that BCRC internalization was insufficient to interrupt the BCRC signaling cascade as evidenced by cell growth inhibition assays. Despite the lack of detectable residual mIgM and CD79αβ on the cell surface, no growth inhibition was observed. These data strongly suggest that signal transduction from mIgM to CD79αβ is not mediated through the PD peptide sequence and internalized BCRC continues to display phosphorylated CD79αβ in its internalized compartment. Upon mAb4-2b binding to a non-ligand binding site on mIgM, mAb4-2b induced both BCRC internalization and in another distinct event, growth inhibition and apoptosis. By competitive mAb studies, the apoptosis mediating conformational epitope appears to be shared, but resides predominantly outside of the linear PD sequence. As mAb4-2b shows increased binding to purified mIgM compared to the linear mIgM-PD peptide and its binding is not substantially blocked by soluble PD 6-mers, the mAb4-2b target epitope is either conformational, or constant region 4 influences its binding, or its epitope resides predominantly in constant region 4. The experimental results support the use of these monoclonal antibodies for drug/radioisotope targeting vehicles or as a mediator of inhibition of the BCRC signaling pathway. As these agents have a high level of specificity because they do not bind to non-mIgM B-cells, normal lymphocytes and non-lymphatic tissues may be spared toxicity.

Example 1

Generation of Anti-ECPD Hybridoma Panels

To isolate monoclonal antibodies reactive with the target peptides, IgM-EGEVSADEEGFEN (SEQ ID NO: 11) and IgG-ELQLEESCAEAQDGELDG (SEQ ID NO: 12), immunogens carrying these peptides were generated (glutathione-S-transferase (GST)) or purchased (Multiple Antigen Peptide (MAP) (Bio-Synthesis, Lewisville, Tex.) and KLH-peptide (Bio-Synthesis, Lewisville, Tex.)). GST, MAP and KLH constructs were used as immunogenic carrier proteins and sets of mice were immunized with one or combinations of the proteins carrying the target peptide. With initial experiments utilizing Balb/c mice as hosts, it became immediately clear that these peptides were not immunogenic, even with standard commercial adjuvant preparations. Low immunogenicity is consistent with previous efforts to produce anti-mIgM and mIgG PD mAbs, while in contrast, efforts to produce mIgE have resulted in several functionally distinct versions (Poggianella M, et al., J Immunol 177:3597-3605 (2006); Feichter S, et al., J of Immunol 180:5499-5505 (2008)). The first panel of 11 monoclonal antibodies generated from Balb/c mice were deemed too weakly reactive to potentially be of clinical value.

It was discovered that of all the mouse strains tested (Balb/c auto-immune mice strains, etc.), only CD-1 mice were capable of significant immune response to these immunogens. Control free KLH (Sigma-Aldrich, St. Louis, Mo., USA) was also obtained for in vitro assays. In addition, the mIgM and mIgG fractions were collected by Perfect-FOCUS™—membrane protein extraction technology (G Biosciences, St Louis, Mo., USA), which yielded enriched mIgM or mIgG preparations from human cell lines, MC 116 (CRL 1649) (Undifferentiated lymphoma expressing mIgM), CA 46 (CRL 1648) (Burkitt's lymphoma expressing mIgM), ST 486 (CRL 1647) (Burkitt's/CLL like cell line expressing mIgM), HT (CRL 2260) (Diffuse mixed B-cell lymphoma expressing mIgM) or DB (CRL 2289) (Large B-cell lymphoma expressing mIgG) adequate for initial ELISA studies. These enriched fractions of membrane IgM or IgG were used to immunize sets of CD1 mice, which generated the second generation monoclonal antibody mAb4-2b. Using various adjuvants, pre- and post-immunization serum were collected and diluted 1:100 and tested for peptide specific activity with ELISA.

New immunization strategies were developed. Extending the peptides into the μC4 domain 4 region ("extended peptide" 18 mer), to possibly capture conformational epitopes using highly purified target protein for boosts and using CD1 mice and new adjuvants, resulted in six mice with post immunization serum titers of >1:10,000. These mice were selected for hybridoma generation using standard techniques. Four clones were isolated that were active in binding to peptide/extended peptide and membrane extraction fractions of mIgM in ELISA, and two clones were specific for mIgG. The mIgM/mIgG molecules were proven to be expressed by CRL 1647 or CRL 2289, respectively, using primers specific for the two PDs by RT PCR and shown to be present in the cell membrane fraction by Western blot analysis. For further screening purposes, constructs (GST, MAP and KLP+/−peptide or extended peptide) were collected for PD peptide mIgM or mIgG, and also for control peptides such as the common overlapping sequences of mIgE and peptide mIgA. mIgD peptide was used in this part of the analysis as all B-cell extracts contain this peptide as well. Only immunizations with certain combinations of immunogens and boosted with the membrane extract fraction, yielded clones with good reactivity; one IgG2b clone produced by a hybridoma cell line from fusion 117 (mAb1-1) PD-KLH peptide immunization only, two IgG2b clones produced by a hybridoma cell line from fusion 118 (mAb2-2b, mAb3-2b), and one IgG1 clone produced by a hybridoma cell line from fusion 119 (mAb4-2b).

The initial screen of the hybridoma supernatants required reactivity with KLH carrying the appropriate PD peptide mIgM or mIgG, no reactivity with free KLH, normal human serum, purified preparation of IgM and KLH carrying peptides for IgE, IgD and IgA. To test cell extracts of CRL 1647-mIgM and CRL 2289-mIgG, a specific "murine Ig-adsorbed" goat anti-human IgMFc or goat anti-IgGFc antisera capture antibody was attached to solid phase plastic. The NP-40 lysate of CRL 1647 or CRL 2289 or control human serum or control breast cancer cell lysate BT-474 was bound to the wells. The CRL 1647 lysate provided human mIgM and CRL 2289 provided human mIgG to bind the capture antibody and the wells were then washed three times. Hybridoma supernatants were then added where "specific" monoclonal antibodies bound to the captured human mIgM or mIgG, which was bound by the plastic bound captured anti-human IgMFc or IgGFc, to form a goat anti-human-IgMFc-mIgM-mAb complex or goat anti-human-IgGFc-mIgG-mAb complex. The mouse mAb was then detected with specific goat anti-mouse Ig HRP labeled (preabsorbed with human IgM or human IgG). Other positive cell extracts, such as Namalwa (CRL 1432) and CA 46 (CRL 1648), yielded similar results.

Monoclonal antibodies collected into a panel included monoclonal antibodies designated mAb1-1, mAb2-2b, mAb3-2b, mAb4-2b, and mAb11-1. Monoclonal antibody mAb1-1 is an IgG2b isotype. Monoclonal antibody mAb1-1 was produced by a hybridoma cell line from fusion 117. Monoclonal antibodies mAb2-2b and mAb3-2b are IgG2b isotypes and mAb4-2b is an IgG1 isotype. Class switch variants were developed to attain IgG1 isotypes for certain experiments to diminish non-specific cell Fc receptor binding present both on target cells and in cell extracts. Monoclonal antibodies mAb 2-2b and mAb3-2b were produced by a hybridoma cell line from fusion 118, and mAb4-2b was produced by hybridoma cell line from fusion 119. Monoclonal antibody mAb11-1 is an IgG1 isotype. Monoclonal antibody mAb11-1 was produced by a hybridoma cell line from fusion 200 and is reactive with mIgG. A second anti-mIgG mAb was also collected but not used in the experiments described herein.

Specificity of reactivity was further confirmed using human mIgE derived from human B-cell line SK007 (human B-cell line expressing mIgE without mIgM) by NP-40 lysis of SK007 cells and tested with ELISA using specific goat anti-human IgE capture antibody. Taken together, these assays indicated that the monoclonal antibodies panel recognized in ELISA both the synthetic peptide sequence contained in the immunogen and the peptide sequence in the human mIgM or mIgG native protein derived by NP-40 lysis and Perfect-FOCUS™ fraction. To check that they did not react with transmembrane or cytoplasmic domains, fluorescent microscopy (FM) of viable cells using fluorescent labeled goat anti-mouse Ig pre-absorbed with mIgM expressing CLL (chronic lymphocytic leukemia) cells, was used to detect mAb bound to viable CLL cells. Results demonstrated mAb specific, but weak cell membrane, staining as expected and similar to anti-light chain activity, indicating low level mIgM cell surface expression. In general, CLL cells express low quantities of BCRC compared to most B-cell lymphomas. Typically, in the clinic, CLL cells are determined to be monoclonal populations and hence malignant, by typing the light chain of mIgM as kappa or lambda. However, it appeared that all four clones did bind to intact viable cells appropriately in the Hemadsorption assays as they were strongly positive with all mIgM+ cell lines tested.

In addition, CLL cells cultured in the presence of these monoclonal antibodies demonstrated increased complexity by side scatter plots in Flow Cytometry compared to controls or polyclonal anti-IgM, suggesting a possible novel cellular effect.

As a consequence of this initial screening strategy, the clones in the panel had the following characteristics: positive in ELISA for: (1) KLH-peptide/extended peptide (mIgM) and (2) reactive with NP-40 lysates of positive expressing cell lines CA46 (CRL 1648) and Namalwa (CRL1432) using capture anti-human IgMFc. The clones were all negative in ELISA with (1) KLH alone, (2) KLH with irrelevant peptide, (3) breast cancer cell line BT-474 NP-40 lysate using capture anti-human IgMFc, (4) human serum using capture anti-human IgMFc, (5) human Waldenstrom's Macroglobulinemic serum using capture anti-human IgMFc, and (6) lysate of SP2/0 mouse myeloma cell line and H2.8 (CRL 2568) mouse myeloma cell line as controls (HRP-labeled mAb). However, testing by ELISA reactivity to the membrane extract of CA 46 (Perfect-FOCUS™, G-Biosciences, St. Louis, Mo.) and Western blot analysis of CA 46 NP-40 lysate demonstrated differences among the clones in their capability to recognize or bind to their epitopes after extraction by Triton™ X-100 and/or exposure to SDS. This suggested that even for the small peptide target 13 mer or the extended 18 mer, peptide conformational changes were critical for mAb binding. For example, the fact that there were clones that detected the mIgM band on Western blots, positive against KLH-peptide or Perfect-FOCUS™ in ELISA, and were reactive in the Triton™ X-100 ELISA suggests that a subset of these clones recognized an epitope preserved in detergent. In addition, the Western blots were complicated, showing binding to multiple molecular weight bands related to complexes of mIgM and CD79αβ.

As mIgM is expressed at low levels, the Flow Cytometry would not be a reliable methodology to prove negativity, thus scanning electron microscopy was done. As radiolabeling reduced affinity of monoclonal antibodies in some cases (Cesano A, Gayko U, Sem Oncol 30:253-257 (2003)), binding and epitope mapping was accomplished with directly labeled antibodies (HRP, Sigma-Aldrich, St. Louis, Mo., USA) and inhibition with small 6-mer peptides or the extended mIgM PD peptide.

Hybridoma cell lines producing the monoclonal antibodies mAb1-1, mAb2-2b, mAb3-2b and mAb4-2b were deposited on Nov. 12, 2014 with the American Type Culture Collection Patent Depository (10801 University Blvd., Manassas, Va.). The deposits were made under the provisions of the Budapest Treaty on the International Recognition of the Deposit of Microorganisms for the Purpose of Patent Procedure and the Regulations thereunder (Budapest Treaty). The hybridoma cell line producing monoclonal antibody designated mAb1-1 has been given ATCC deposit number PTA-121719. The hybridoma cell line producing monoclonal antibody designated mAb2-2b has been given ATCC deposit number PTA-121717. The hybridoma cell line producing monoclonal antibody designated mAb3-2b has been given ATCC deposit number PTA-121718. The hybridoma cell line producing monoclonal antibody designated mAb4-2b has been given ATCC deposit number PTA-121716.

Example 2

Antibody Purification

Antibody purification was accomplished using protein A sepharose columns (Pierce Inc., Rockford, Ill., USA) with application of supernatants from each hybridoma line at pH 8.6 in Tris solution. Further washing was done in PBS at pH 7.0 and then eluting mIgM at pH 4.0. Sterile filtered monoclonal antibodies were stored at 4° C. at 500 micrograms/ml in sterile PBS with/without azide. Antibody preparations for ADCC, Complement lysis, growth inhibition assay and biologic assays were sterile filtered in PBS without azide at 1000 micrograms/ml.

Example 3

Antibody Immune-Affinity Purification of mIgM

Antibody purification of mIgM was accomplished using mAb1-1 or mAb1-1 with mAb2-2b and mAb3-2b covalently bound immune-affinity beads (Pierce Inc., Rockford, Ill., USA), application of CRL-1648 NP-40 extract and then washing beads at pH 8.6 in Tris solution. Further washing was done in PBS at pH 7.0 and then eluting mIgM at pH 4.0. Sterile filtered mIgM batches were stored at 4° C. at 500 micrograms/ml in sterile PBS with/without azide.

Example 4

Specificity Analysis

Hemadsorption tests of the panel of antibodies against an epithelial cell-line bank was done to eliminate clones with non-specific cross reactivity (Rettig W J, et al., Int J Cancer 58:385-392 (1994); Kitamura K, et al., Proc Natl Acad Sci USA 91:12957-12961 (1994); Garin-Chesa P, et al., Int J Oncol 9:465-471 (1996); Rader C, et al., J Biol Chem 275; 13668-13676 (2000)). A subset of these epithelial cell lines had been tested by RT-PCR for PD sequence to define true negatives, however, mIgM has never been reported to be expressed by malignant cells other than those of B-cell lineage and the studies herein did not reveal these sequences in any of the cell lines in the panel. This observation was extended by RT-PCR of a panel of melanomas and sarcomas for the PD 13-mer mIgM and 18-mer mIgG and found no signal demonstrating expression of this peptide in these non-B-cell lineage cells. Thus, any binding would represent cross reactivity and not BCRC antigen detection. The binding of antibodies to cell surfaces of tumor cells was detected microscopically by adsorption of erythrocytes coated with anti-mouse Ig antibody or protein A. The titer was defined as the highest dilution of reagent giving maximum rosetting (Rettig W J, et al., Int J Cancer 58:385-392 (1994); Kitamura K, et al., Proc Natl Acad Sci USA 91:12957-12961 (1994); Garin-Chesa P, et al., Int J Oncol 9:465-471 (1996); Rader C, et al., J Biol Chem 275:13668-13676 (2000)). Control positive antibodies were contained in a panel of antibodies previously developed by applicants and colleagues, including mAb A33, mAb 3S193, mAb G250 and mAb F19 (Rettig W J, et al., Int J Cancer 58:385-392 (1994); Kitamura K, et al., Proc Natl Acad Sci USA 91:12957-12961 (1994); Garin-Chesa P, et al., Int J Oncol 9:465-471 (1996); Rader C, et al., J Biol Chem 275:13668-13676 (2000)). Extensive screening of monoclonal antibodies mAb1-1, mAb2-2b, mAb3-2b and mAb4-2b in binding assays against a panel of human epithelial cell lines: breast (9), lung (9), colon (12), renal (6), prostate (3), ovary (3), melanoma (6) and sarcoma (2) were all negative.

CRL 1647 was a true positive that is weakly plastic adherent but rendered more adherent by pre-coating plates with poly L-lysine. For non-adherent target cells, rosetting was assessed by microscopically examining cells on glass slides.

Example 5 mAb Specific Reactivity with Viable Cell Lines and NP-40 Lysate Assays

Hem-adsorption assays (HA) using protein G coated huRBCs were scored using phase contrast microscopy (100×) as negative (neg), +, ++, or +++. The cell line panel consisted of (1) mIgM-lambda, CRL 1432, CRL 1596, CRL 1649, CRL 3006, CRL 2958, (2) mIgM-kappa, CRL 1647, CRL 1648, CRL 2260, (3) mIgG-lambda 2289, (4) mIgG, CRL 2632, and (5) SK007. Epithelial cancer and melanoma cell lines were selected for reactivity with isotype-matched control mAbs. ESA of CL (ELISA sandwich assay of cell lysates) was performed using a mouse Ig pre-adsorbed capture goat anti-human IgM constant region serum and detected with a human Ig pre-adsorbed goat anti-mouse Ig-HRP. Of note is that all lymphoma lines have cytoplasmic IgM similar to serum IgM. Thus, this assay does not confirm or assess mAb specificity to distinguish reactivity between mIgM vs. serum or cytoplasmic IgM. Results are demonstrated in Table 4 below.

TABLE 4

| | mAb 1 | mAb 2 | mAb 3 | mAb 4 | mAb Isotype IgG1 control | mAb Isotype IgG2 control |
|---|---|---|---|---|---|---|
| HA Cell targets | | | | | | |
| mIgM-kappa | +++ | +++ | +++ | +++ | neg | neg |
| mIgM-lambda | +++ | +++ | +++ | +++ | neg | neg |
| mIgG-kappa | neg | neg | neg | neg | neg | neg |
| mIgG-lambda | neg | neg | neg | neg | neg | neg |
| mIgE | neg | neg | neg | neg | neg | neg |
| Colon (12) | neg | neg | neg | neg | +++ | +++ |
| Breast (9) | neg | neg | neg | neg | ++/+++ | neg |
| Lung (9) | neg | neg | neg | neg | ++/+++ | neg |
| Melanoma (2) | neg | neg | neg | neg | ++/+++ | neg |
| ESA of CL Cell targets | | | | | | |
| mIgM-kappa | +++ | +++ | +++ | +++ | neg | neg |
| mIgM-lambda | +++ | +++ | +++ | +++ | neg | neg |
| mIgG-kappa | neg | neg | neg | neg | neg | neg |
| mIgG-lambda | neg | neg | neg | neg | neg | neg |
| mIgE | neg | neg | neg | neg | neg | neg |
| Colon (12) | neg | neg | neg | neg | +++ | +++ |
| Breast (9) | neg | neg | neg | neg | +++ | neg |
| Lung (9) | neg | neg | neg | neg | +++ | neg |
| Melanoma (2) | neg | neg | neg | neg | +++ | neg |

Statistical analysis: Student's t-test was used to assess statistical validity of Elisa data points shown. All data points consist of 12 wells in each of 3 experiments performed, and representative average values are shown. Data for mAb 1, mAb 2, mAb 3, and mAb 4 were demonstrated to exceed $p<0.5$ for all, +++ or ++ compared to their respective controls. Values that are bolded are statistically significant.

Cell lines: Positive cell lines were authenticated by acquisition from the ATCC and are shown in the first 5 rows of each assay, which are identified as follows: mIgM-kappa=CRL 1647, CRL 1648, CRL 2260; mIgM-lambda=CRL 1432, CRL 1596, CRL 1649, CRL 2958, mIgG-kappa=CRL 2632; mIgG-lambda=CRL 2289; mIgE=SK007. Colon, breast, lung and melanoma cell lines were obtained from the ATCC and tested serologically to confirm their identity. This non-lymphoid cancer cell line panel of colon, breast, lung and melanoma cell lines consisted of the following cell lines:
  (1) Colon: T84, SW1222, Colo 205, Lim 1215, HT-29, DLD-1, SW1116, SW 620, SW 480, LoVo, HCT-15, HCT-116
  (2) Breast: BT 474, SK BR7, CaMa-1, BT-20, MCF-7, SK Br-3, MDA-MB 453, MDA-MB 436, MDA-MB 468.
  (3) Lung: H64, SW1271, DMS 78, SK-LU-9, NCI H596, A549, NCI H1105, NCI H69, DMS 53
  (4) Melanoma: SK MEL-29, MeWo

Example 6

Relative Binding Studies

Using the ELISA assay as described above, purified monoclonal antibodies mAb1-1, mAb2-2b, mAb3-2b, mAb4-2b, and mAb11-1 were serially diluted 1:4, then were added to bind to the human mIgM bound by the capture anti-human IgM. The bound mouse mAb was then detected with specific goat anti-mouse Ig-HRP labeled reagent. Monoclonal antibodies of the same isotype could be compared to each other. Similar assays were carried out with other positive targets identified in Tables 5-8 below.

ELISA Assays

TABLE 5 mAb Molecular Specificity and Relative Reactivity by Direct Binding

| | ELISA reading | | | | | | | | |
|---|---|---|---|---|---|---|---|---|---|
| | KLH-PDm | KLH | KLH-PDg | CA 46 | SU-DHL-5 | CRL-1596 | CRL-1432 | CRL-1647 | CRL-1642 |
| mAb1-1 | >4.0 | 0.3 | 0.3 | 3.7 | >4.0 | 3.2 | 3.5 | 2.9 | 3.0 |
| mAb2-2b | 3.7 | 0.2 | 0.4 | 3.4 | 3.4 | 3.4 | 3.2 | 3.1 | 3.3 |
| mAb3-2b | 3.3 | 0.3 | 0.3 | 3.1 | 2.7 | 3.1 | 3.2 | 2.8 | 2.8 |
| mAb4-2b | 0.9 | 0.3 | 0.2 | >4.0 | 3.8 | >4.0 | >4.0 | 3.9 | 3.7 |
| mAb11-1 | 0.3 | 0.3 | 3.2 | 0.3 | 0.2 | 0.3 | >4.0 | 0.2 | 0.2 |
| Anti-huIgM | 0.2 | 0.2 | 0.2 | 3.8 | >4.0 | >4.0 | >4.0 | >4.0 | >4.0 |

TABLE 6 mAb Molecular Specificity and Relative Reactivity by Direct Binding

| | mAb 1 | mAb 2 | mAb 3 | mAb 4 | mAb control | mAb control |
|---|---|---|---|---|---|---|
| mIgM-PD-KLH | >4.0 | >4.0 | >4.0 | 0.5 | 0.1 | 0.1 |
| KLH | 0.1 | 0.1 | 0.1 | 0.1 | 0.1 | 0.1 |
| mIgM-PD-MAP | >4.0 | >4.0 | >4.0 | 0.9 | 0.1 | 0.1 |
| MAP | 0.2 | 0.2 | 0.2 | 0.1 | 0.1 | 0.1 |
| mIgM-PD | >4.0 | >4.0 | >4.0 | 0.8 | 0.1 | 0.1 |
| mIgG-PD | 0.1 | 0.2 | 0.2 | 0.1 | 0.1 | 0.1 |
| P-Focus | 3.1 | 2.8 | 2.6 | >4.0 | 0.3 | 0.2 |
| P-Focus + IA | 3.3 | 2.5 | 2.3 | >4.0 | 0.1 | 0.1 |
| mIgM-PD-Isomer 1 | 3.8 | 3.2 | 3.0 | 0.9 | 0.1 | 0.1 |
| MIgM-PD-Isomer 2 | 3.2 | 3.0 | 3.2 | 0.7 | 0.1 | 0.1 | mIgM-PD = EGEVSADEEGFEN (SEQ ID. NO: 11)
Isomer 1 = EGENSADEEGFEN (SEQ ID NO: 14)
isomer 2 = EGEVSEDEEGFEN (SEQ ID NO: 15)

Statistical analysis: Student's t-test was used to assess statistical validity of data points shown. All data points consist of 12 wells in each of 3 experiments performed, and representative average values are shown. Data for mAb 1, mAb 2, mAb 3, and mAb 4 were demonstrated to exceed $p<0.5$ for rows 1, 3 5, 7, 8, 9 and 10 compared to their respective controls. Values that are bolded are statistically significant. Abbreviations: PD, proximal domain; mIgM, membrane bound IgM; KLH, keyhole limpet hemocyanin; MAP, multiple antigen peptide (of PD); P-Focus™, Perfect FOCUS™ cell extract; IA, immune-affinity column (mAb 1).

TABLE 7 mAb Molecular Specificity and Relative Reactivity by Inhibition of Direct Binding

| | ELISA Reading | | | | | | | | |
|---|---|---|---|---|---|---|---|---|---|
| | CRL-2632 | Serum normal | Purified IgM | Serum W.M. | Purified mIgM | Purified mIgM blocked by KLH-PDm | Purified mIgM blocked by KLH-PDg | Purified mIgM blocked by KLH | Purified mIgM blocked by COLO-205 |
| mAb1-1 | 0.2 | 0.2 | 0.3 | 0.3 | >4.0 | 0.7 | >4.0 | 3.9 | 3.7 |
| mAb2-2b | 0.3 | 0.3 | 0.4 | 0.3 | 3.4 | 0.3 | 3.6 | 3.5 | 3.5 |
| mAb3-2b | 0.3 | 0.3 | 0.3 | 0.3 | 3.6 | 0.4 | 3.7 | 3.6 | 3.4 |
| mAb4-2b | 0.3 | 0.3 | 0.3 | 0.2 | >4.0 | 3.8 | >4.0 | 3.8 | 3.9 |
| mAb11-1 | 3.5 | 0.4 | 0.2 | 0.3 | 0.4 | 0.3 | 0.3 | 0.4 | 0.2 |
| Anti-huIgM | 0.7 | >4.0 | >4.0 | >4.0 | >4.0 | >4.0 | >4.0 | >4.0 | 3.9 |

KLH-PDm = keyhole limpet hemocyanin-Proximal Domain peptide for IgM
KLH = keyhole limpet hemocyanin
KLH-PDg = keyhole limpet hemocyanin-Proximal Domain Peptide for mIgG
CA 46, SU-DHL-5, CRL-1592, CRL-1432, CRL-1647, CRL-1642 = mIgM + B-cell lines
CRL-2632 = mIgG + B-cell line
Serum W.M. = Serum from patient with Waldenstrom's Macroglobulinemia
Purified mIgM = Immune-Affinity purified mIgM from CA 46 using mAb1-1
COLO-205 = Human colon cancer cell line
mAb11-1 = monoclonal antibody to PD of mIgG
Anti-huIgM = mouse polyclonal antibodies to human IgM

TABLE 8

Serum and Cell Inhibition of mAb Binding to purified mIgM cell extract CRL 1647

|  | Blank FCS | Normal serum | Normal plasma | CLL serum | CLL cells | W-Ms serum | DLBCL serum | INHL serum | Breast serum | Colon serum |
|---|---|---|---|---|---|---|---|---|---|---|
| mAb 1 | +++ | +++ | +++ | +++ | 0 | +++ | +++ | +++ | +++ | ++++ |
| mAb 2 | +++ | +++ | +++ | +++ | 0 | +++ | +++ | +++ | +++ | +++ |
| mAb 3 | +++ | +++ | +++ | +++ | 0 | +++ | +++ | +++ | +++ | +++ |
| mAb 4 | +++ | +++ | +++ | +++ | 0 | +++ | +++ | +++ | +++ | +++ |
| Anti-hu-IgM | +++ | + | + | ++ | ++ | 0 | + | + | + | + |

+++ = no inhibition detected
0 = complete inhibition

Inhibition of mAb binding to Perfect FOCUS™ target cell extract by serum, plasma and CLL cells demonstrated lack of specific antigen in blood capable of blocking mAb binding to target antigen while, in contrast, CLL cells adsorbed mAb thereby reducing mAb binding to target.

Statistical analysis: Student's t-test was used to assess statistical validity of data points shown. All data points consist of 12 wells in each of 3 experiments performed, and representative average values are shown as a score of 0 to +++. Data for mAb 1, mAb 2, mAb 3, and mAb 4 demonstrated no significant reduction of binding except for pre adsorption by CLL cells. These results were significantly different from polyclonal anti-human IgM shown in the bottom row, exceeding p<0.5 for normal serum, normal plasma, Waldenstrom's Macroglobulenemia sera and lymphoma breast or colon cancer serum. Scoring shown, +++=no statistical reduction of binding, ++=p>0.05 reduction, +=p>0.01 and 0=no detectable binding over background. Serum tested included Waldenstrom's Macroglobulenemia serum (W-Ms) that contained 4.2 grams/deciliter IgM, CLL serum that contained 22 mg/deciliter of IgM, Diffuse Large Cell B-cell Lymphoma ABC type (DLBCL) Indolent non-Hodgkin's lymphoma (INHL).

Example 7

Binding Studies and Epitope Mapping by Peptide Inhibition

In initial radiolabeling studies, the IgG2b monoclonal antibodies did not label well by radioimmunoreactivity assays (Barendswaard E C, et al., Int J Oncol 12:45-53 (1998); Barendswaard E, et al., J Nucl Med 42:1251-1256 (2001); Scatchard plots www.curvefit.com/scatchard_plots.htm#transforming_data_to_create_a_scatchard). Protein labeling kits for HRP (Sigma-Aldrich, St Louis, Mo., USA; Pierce Chemicals, Rockford, Ill., USA) were used in a solid phase labeling technique. Using excess unlabeled antibody to block labeled antibody binding defined the following groups of clones: 1. those blocking the labeled antibody (same epitope), 2. those not blocking the epitope (different epitope) and 3. partial blocking (a near epitope or weaker binder). This process was repeated until all the clones were epitope defined. Additional information was obtained through inhibition assays where the mAb was blocked by 6-mers and this data was confirmatory. The results of the binding studies are presented in Tables 9 and 10 below.

TABLE 9

Molecular Epitope Mapping by Competitive mAb Binding

|  | mAb 1 | mAb 2 | mAb 3 | mAb 4 | Control mAb |
|---|---|---|---|---|---|
| Blocked by mAb 1 |  |  |  |  |  |
| mIgM-PD | 11 | 88 | 82 | 72 | neg |
| mIgG-PD | neg | neg | neg | neg | neg |
| KLH-mIgM-PD | 6 | 94 | 92 | 74 | neg |
| mIgM-PD-KLH | 10 | 92 | 91 | 52 | neg |
| P-Focus + IA | 13 | 90 | 89 | 96 | neg |
| Blocked by mAb 2 |  |  |  |  |  |
| mIgM-PD | 80 | 2 | 23 | 69 | neg |
| mIgG-PD | neg | neg | neg | neg | neg |
| KLH-mIgM-PD | 67 | 4 | 24 | 68 | neg |
| mIgM-PD-KLH | 78 | 2 | 34 | 71 | neg |
| P-Focus + IA | 78 | 3 | 31 | 96 | neg |
| Blocked by mAb 3 |  |  |  |  |  |
| mIgM-PD | 85 | 35 | 9 | 63 | neg |
| mIgG-PD | neg | neg | neg | neg | neg |
| KLH-mIgM-PD | 79 | 28 | 4 | 72 | neg |
| mIgM-PD-KLH | 87 | 36 | 9 | 62 | neg |
| P-Focus + IA | 82 | 39 | 10 | 85 | neg |
| Blocked by mAb 4 |  |  |  |  |  |
| mIgM-PD | 93 | 87 | 84 | 12 | neg |
| mIgG-PD | neg | neg | neg | neg | neg |
| KLH-mIgM-PD | 82 | 88 | 95 | 14 | neg |
| mIgM-PD-KLH | 90 | 94 | 85 | 9 | neg |
| P-Focus + IA | 95 | 94 | 86 | 9 | neg |

Statistical analysis: Student's t-test was used to assess statistical validity of data shown. All data points consist of 12 wells in each of 3 experiments performed, and representative average values are shown. Statistical significance comparisons include for mIgM-PD, KLH-mIgM-PD and P-Focus+IA each in a test of mAb-HRP reactivity pre-blocked by unlabeled mAb (e.g., mAb1-1-HRP was blocked by unlabeled mAb1-1 and similar results for each HRP labeled mAb by its partner mAb, bolded). Data points for mAb 1, mAb 2, mAb 3, and mAb 4 were demonstrated to exceed p<0.5 for each self-blocking vs unblocked (data not shown). Further tests demonstrated mAb 1 did not block mAb 2, mAb 3 or mAb 4; mAb 2 did not block mAb 1 and mAb 4; but mAb 3 was partially reduced compared to mAb 1 and mAb 4. These results were similar for mAb 3 analysis showing partial blocking of mAb 2. mAb 4 analysis demonstrated lack of blocking of mAb1, mAb 2 and mAb 4. Conclusions: For mIgM-PD, KLH-mIgM-PD and P-Focus+IA targets, mAb 1 and mAb 4 each detected a distinct epitope while mAb 2 and mAb 3 detected another defined epitope that is partially shared. mAb 4 showed relative improved binding to purified mIgM (P-Focus+IA) when compared to the other mAbs.

TABLE 10

Molecular Epitope Mapping by Competitive 6-mer peptide Binding

| Blocked by 6-mer A | mAb 1 | mAb 2 | mAb 3 | mAb 4 | Control mAb |
|---|---|---|---|---|---|
| mIgM-PD | 28 | 45 | 61 | 81 | neg |
| mIgG-PD | neg | neg | neg | neg | neg |
| P-Focus | 19 | 53 | 54 | 90 | neg |
| Blocked by 6-mer B | mAb 1 | mAb 2 | mAb 3 | mAb 4 | Control mAb |
| mIgM-PD | 84 | 57 | 50 | 70 | neg |
| mIgG-PD | neg | neg | neg | neg | neg |
| P-Focus | 90 | 48 | 57 | 94 | neg |

6-mer A peptide=EGEVSA (SEQ ID NO: 16) and 6-mer peptide B=EEGFEN (SEQ ID NO: 17) were used in molar excess X100 compared to mAb-HRP. Statistical analysis demonstrates that mAb 4 detected a distinct epitope not blocked by either A or B 6-mer. While mAb1 was not blocked by B, mAb 1 was strongly blocked by A and mAb 2 and mAb 3 were partially blocked by both A and B. Limiting factors in peptide inhibition assays included hydrophobicity characteristics of small peptides fragments.

These studies indicate that mAb 4-2b had increased binding to the extended peptide compared to the 11-mer, but neither 6-mer completely blocked it. These data suggest that its epitope straddles the ECPD and the terminal mu domain 4 and that its epitope is conformational and thus not completely inhibited by the small linear peptides. Of note, the antibody, mAb4-2b, was strongest in the hemadsorption assay and FM.

The other 3 mAbs, mAb1-1, mAb2-2b and mAb3-2b split into two epitopes, one proximal and one distal, within the ECPD, despite the fact that there was always some degree of partial blocking with the HRP labeled experiments. While binding to 3 distinct epitopes could be defined, overlap (partial blocking) does exist. Epitope-specific clones with the highest avidity and restrictive specificity of this final panel of 4 mAbs, each detecting an epitope within the extended ECPD as determined by peptide inhibition were collected into an "epitope panel" of 3 monoclonal antibodies.

Example 8

Binding Studies by Scanning Immuno-Electron Microscopy

Figure 1B:
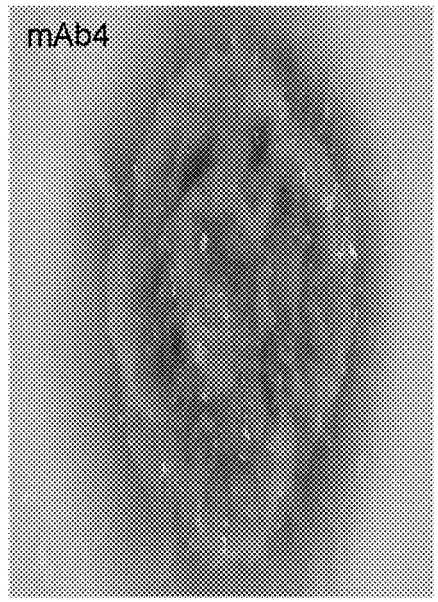
Figure 1C:
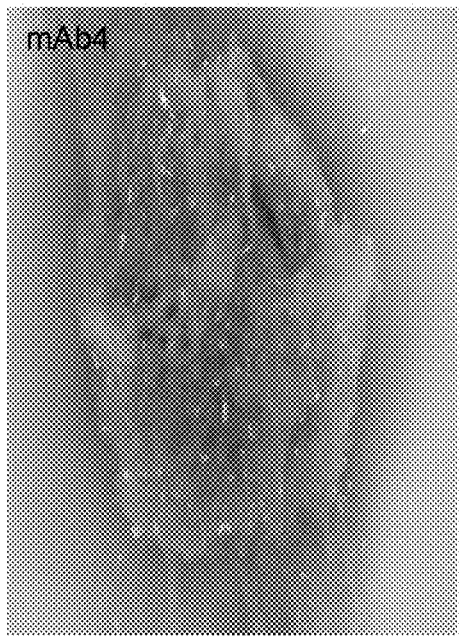
Figure 1D:
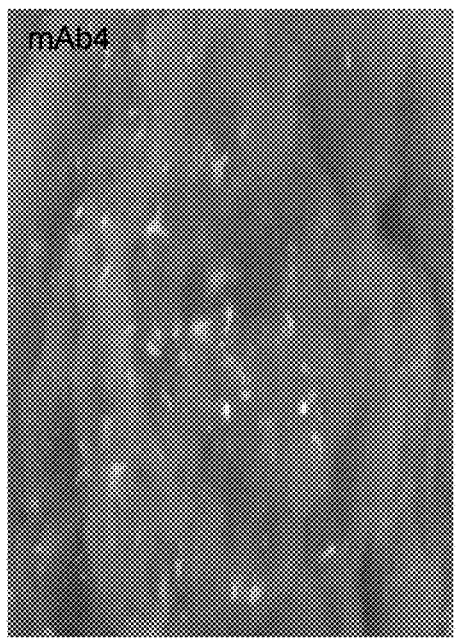

Cell line CA 46 (CRL 1648) represents a B-cell cell line with relatively low mIgM expression based on "DIM" light chain reactivity by flow cytometric analysis, similar to chronic lymphocytic leukemia (CLL) cells, and was used in Scanning Immuno-Electron microscopy (SEM) to study the binding of the monoclonal antibodies. SEM results are presented in Tables 11 to 18 below. The micrograph in FIG. 1A shows the control-IgG2b isotype matched control antibody plus secondary goat anti-mouse Ig-gold. The micrographs in FIGS. 1B and 1C show monoclonal antibody m-Ab4-2b, designated mAb4 in the micrograph, binding to two different cells of CA 46 (CRL 1648) at the same magnification as the control antibody in FIG. 1A. The micrograph in FIG. 1D shows monoclonal antibody m-Ab4-2b, designated mAb4 in the micrograph, binding to a third CA 46 (CRL 1648) cell at a higher magnification compared to the control antibody of FIG. 1A. Bright white spots represent immune gold particles-goat anti-mouse Ig reacting with the mAb4 monoclonal antibody on the cell surface. No background goat anti-mouse Ig reactivity was seen with the control antibody in FIG. 1A, indicating lack of cross-reactivity with human mIgM and lack of non-specific binding by Fc receptors on B-cells. From these micrographs, it was estimated that mIgM was present at 5,000-10,000 molecules per cell. These SEM micrographs show that mAb4-2b binds to the mIgM on the cell surface.

TABLE 11

| Target Cell Line: CA 46 (CRL 1648) Glutaraldehyde fixation Antibody Tested | Scanning Immuno-Electron Microscopy (SEM) Cell Line Binding Results |
|---|---|
| mAb1-1 | Positive |
| mAb2-2b | Positive |
| mAb3-2b | Positive |
| mAb4-2b | Positive |
| Mouse anti-human IgM | Positive |
| Mouse anti-human Kappa light chain | Positive |
| mAb anti-human IgM heavy chain | Positive |
| mAb anti-human IgG heavy chain | Negative |

Direct mAb binding studies demonstrated cell surface binding and the presence of target mIgM was shown by anti-human IgM, anti-human Kappa light chain, anti-human IgM heavy chain reagents.

TABLE 12

| Target Cell Line: CA 46 (CRL 1648) Glutaraldehyde fixation Pre-incubation of antibody with human serum 1:10 or human Waldenstrom's Macroglobuinemia serum 1:10 (4.4 gms IgM/dl) Antibody Tested | Scanning Immuno-Electron Microscopy (SEM) Cell Line Binding Results |
|---|---|
| mAb1-1 | Positive |
| mAb2-2b | Positive |
| mAb3-2b | Positive |
| mAb3-2b | Positive |
| Mouse anti-human IgM | Negative |
| Mouse anti-human kappa light chain | Negative |
| mAb anti-human IgM heavy chain | Negative |
| mAb anti-human IgG heavy chain | Negative | mAbs were not blocked from cell surface binding by pre-incubation with human Waldenstrom's serum containing high levels of serum IgM. In contrast, anti-human IgM, anti-human Kappa light chain, and anti-human IgM heavy chain reagents were blocked, resulting in their lack of cell surface binding.

TABLE 13

| Target Cell Line: CA 46 (CRL 1648) Glutaraldehyde fixation; Pre incubation of antibody with excess CRL-1432 (adsorption) (mIgM positive cell line) Antibody Tested | Scanning Immuno-Electron Microscopy (SEM) Cell Line Binding Results |
|---|---|
| mAb1-1 | Negative |
| mAb2-2b | Negative |
| mAb3-2b | Negative |
| mAb4-2b | Negative |
| Mouse anti-human IgM | Negative |
| mAb anti-human IgM heavy chain | Negative |
| mAb anti human IgG Heavy chain | Negative | mAbs were blocked from cell surface binding by pre-incubation with mIgM expressing CRL 1432, and anti-human IgM, anti-human Kappa light chain, anti-human IgM heavy chain reagents were blocked as they also bind to mIgM on CRL 1432.

TABLE 14

Target Cell Line: CA 46 (CRL 1648)
Glutaraldehyde fixation;
Pre incubation of antibody with excess
Proximal Domain peptide for mIgM

| Antibody Tested | Scanning Immuno-Electron Microscopy (SEM) Cell Line Binding Results |
|---|---|
| mAb1-1 | Negative |
| mAb2-2b | Negative |
| mAb3-2b | Negative |
| mAb4-2b | Positive |
| Mouse anti-human IgM | Positive |
| mAb anti-human IgM heavy chain | Positive |
| mAb anti-human IgG heavy chain | Negative |

Excess mIgM PD blocked mAb 1-1, mAb2-2b and mAb3-2b binding to the cell surface of CRL 1648, whereas mAb4-2b was not blocked and could be detected binding to the CRL1648 cell surface.

TABLE 15

Target Cell Line: CA 46 (CRL 1648)
Pre-incubation of CA 46 cells with mAb1-1 at 37° C. for 30 minutes, followed by glutaraldehyde fixation, followed by antibody incubation and then SEM

| Antibody Tested | Scanning Immuno-Electron Microscopy (SEM) Cell Line Binding Results |
|---|---|
| mAb1-1 | Negative |
| mAb2-2b | Negative |
| mAb3-2b | Negative |
| mAb4-2b | Negative |
| Mouse anti-human IgM heavy chain | Negative |
| Mouse anti-human IgG heavy chain | Negative | mAb1-1 mediated internalization of mIgM by 30 minutes, resulting in lack of detection of mIgM on the surface of CRL 1648 cells by mAbs or anti-human IgM heavy chain reagent.

TABLE 16

Target Cell Line: CA 46 (CRL 1648)
Pre-incubation of CA 46 cells with mAb4-2b at 37° C. for 30 minutes followed by glutaraldehyde fixation and then SEM

| Antibody Tested | Scanning Immuno-Electron Microscopy (SEM) Cell Line Binding Results |
|---|---|
| mAb1-1 | Negative |
| mAb2-2b | Negative |
| mAb3-2b | Negative |
| mAb4-2b | Negative |
| Mouse anti-human IgM | Negative |
| Mouse anti-human IgM heavy chain | Negative |
| Mouse anti-human IgG heavy chain | Negative | mAb4-2b mediated internalization of mIgM by 30 minutes, resulting in lack of detection of mIgM on the surface of CRL 1648 cells by mAbs or anti-human IgM heavy chain reagent.

TABLE 17

Target Cell Line: CA 46 (CRL 1648)
Fixation of CA 46 cells with glutaraldehyde followed by incubation with mAb1-1 followed by mAb

| Antibody Tested | Scanning Immuno-Electron Microscopy (SEM) Using Anti-Mouse IgG1 Antibody Gold Cell Line Binding Results |
|---|---|
| mAb1-1 | Negative |
| mAb2-2b | Negative |
| mAb3-2b | Negative |
| mAb4-2b | Positive |
| Mouse anti-human IgM heavy chain | Positive |
| Mouse anti-human IgG heavy chain | Negative |

Anti-mouse IgG1-Gold reagent detected mAb4-2b, which is a mouse IgG1 isotype, bound to the surface of CRL 1648 preincubated with the IgG2b isotype mAb1-1 antibody, indicating that mAb1-1 binds to a different epitope than mAb4-2b and does not block mAb4-2b.

TABLE 18

Target Cell Line: CA 46 (CRL 1648)
Fixation of CA 46 cells with glutaraldehyde followed by incubation with mAb2-2b followed by mAb

| Antibody Tested | Scanning Immuno-Electron Microscopy (SEM) Using Anti-Mouse IgG1 Antibody Gold Cell Line Binding Results |
|---|---|
| mAb1-1 | Negative |
| mAb2-2b | Negative |
| mAb3-2b | Negative |
| mAb4-2b | Positive |
| Mouse anti-human IgM | Positive |
| Mouse anti-human IgM heavy chain | Positive |
| Mouse anti-human IgG heavy chain | Negative |

Anti-mouse IgG1-Gold reagent detected mAb4-2b, which is a mouse IgG1 isotype, bound to the surface of CRL 1648 preincubated with the IgG2b isotype mAb2-2b antibody, indicating that mAb2-2b binds to a different epitope than mAb4-2b and does not block mAb4-2b.

Example 9 mAb Binding Mediates BCRC Internalization

Figure 2A:
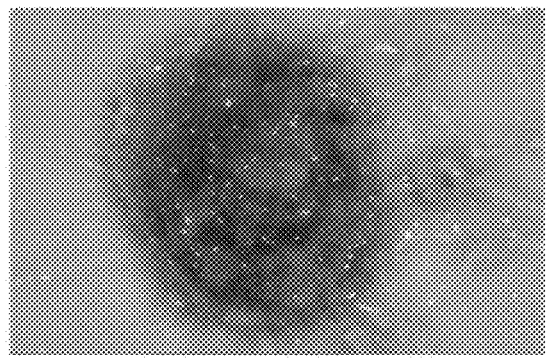
FIGS. 2A-2E. Cell line CRL 1648 Scanning Immuno-Electron microscopy (Burkitt's lymphoma).
Figure 2B:
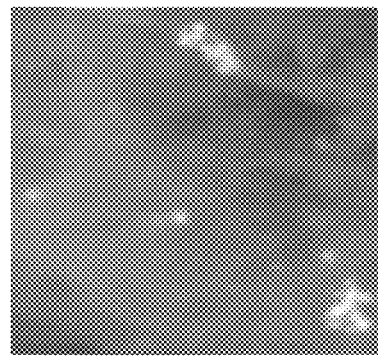
Figure 2C:
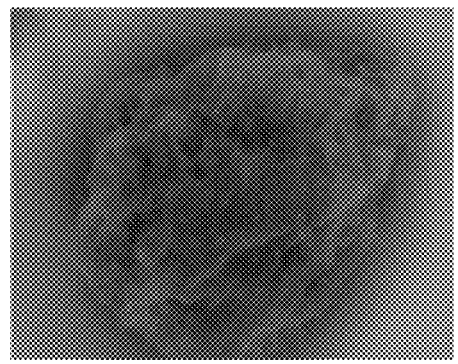
Figure 2D:
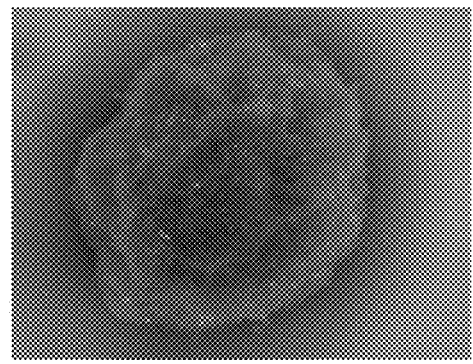
Figure 2E:
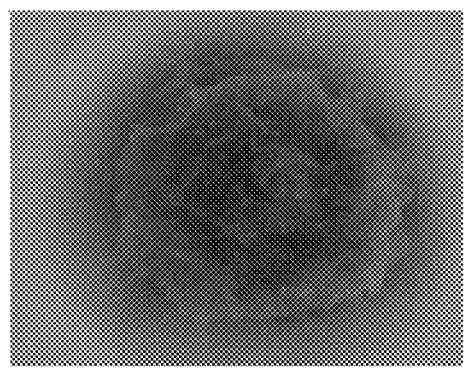
Figure 3:
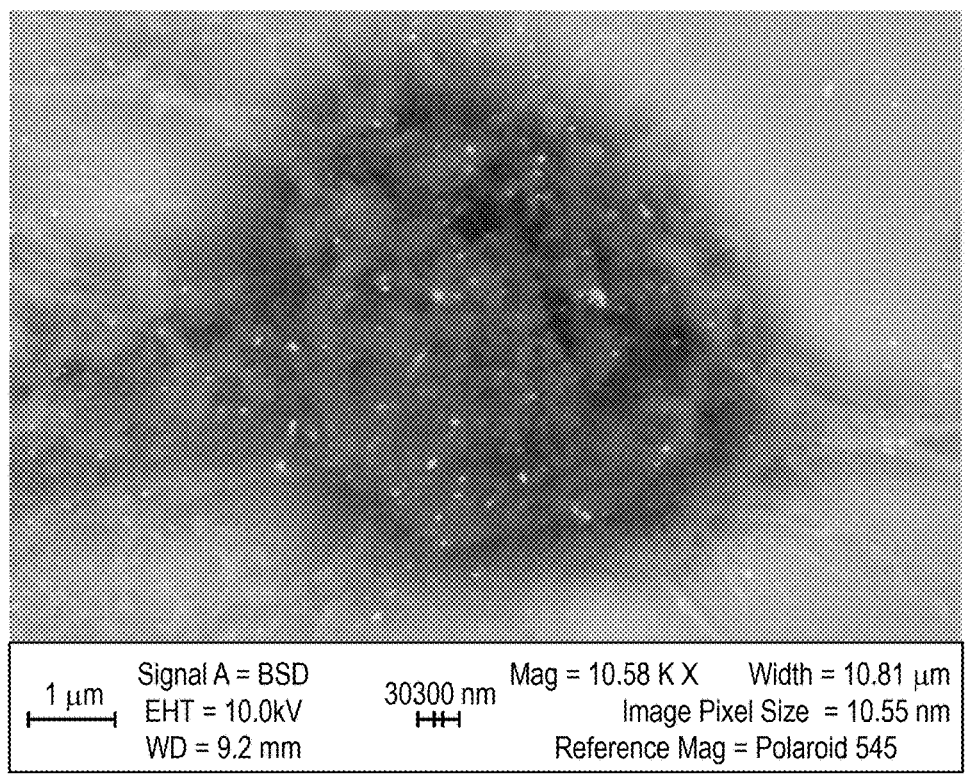
FIG. 3. Cell line CRL 1596 Scanning Immuno-Electron microscopy (Burkitt's lymphoma).
Figures 4A, 4B:
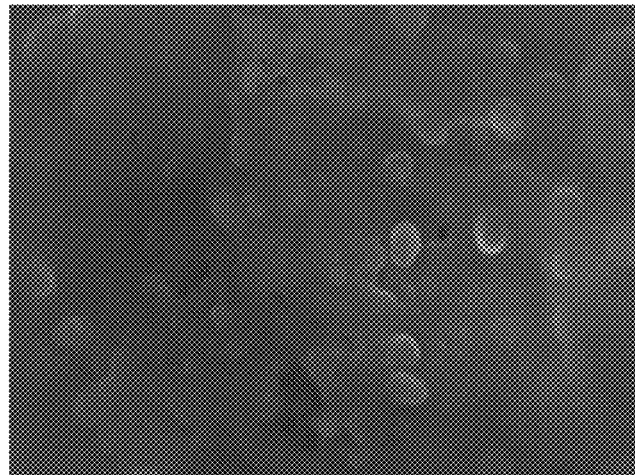
FIGS. 4A-4B. Cell line CRL 2260 Scanning Immuno-Electron microscopy (Diffuse mixed B-cell lymphoma).
Figure 5B:
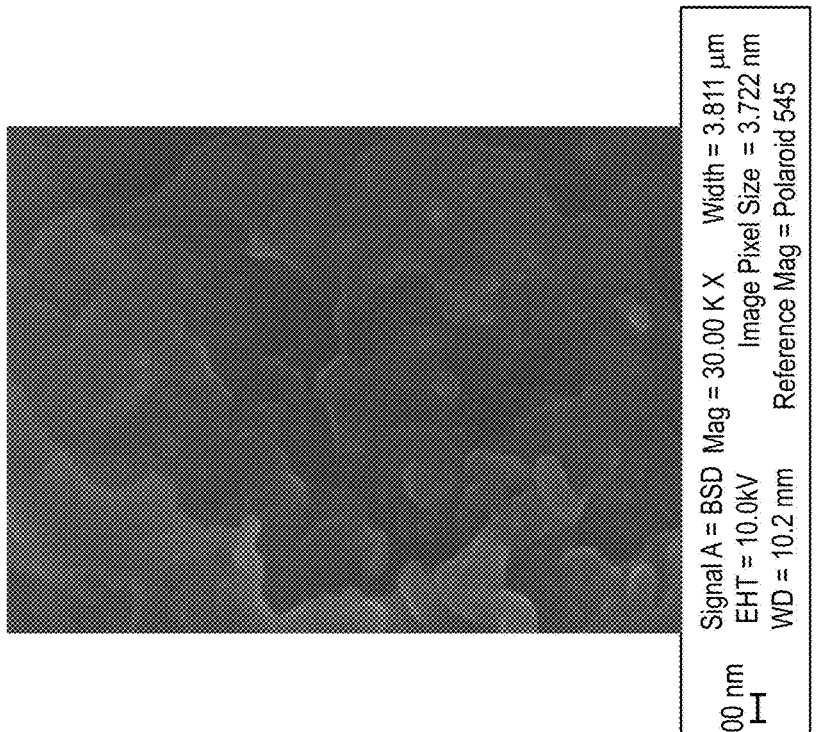
FIGS. 5A-5B. Cell line CRL 3006 Scanning Immuno-Electron microscopy (Mantle cell lymphoma).
Figure 5A:
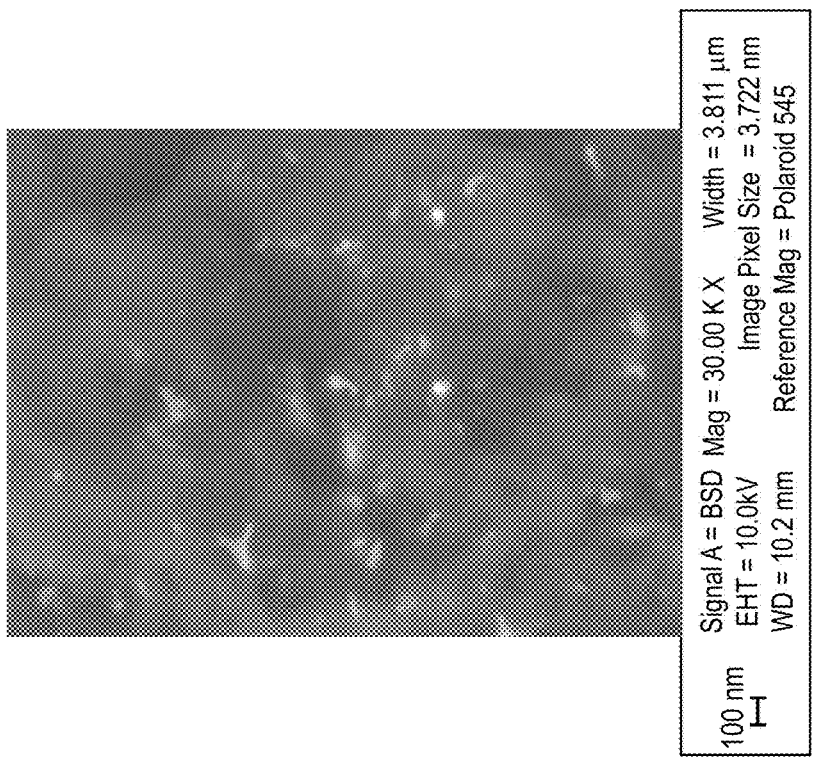

Scanning Immuno-Electron microscopy (SEM) was performed to detect binding of monoclonal antibody mAb 4 to cells of cell line CRL 1648. FIG. 2A shows monoclonal antibody mAb 4 binding to a glutaraldehyde fixed CRL 1648 cell. FIG. 2B shows mAb 4 binding to micro-clusters of BCRC. When CRL 1648 cells were incubated with mAb 4 at 37° C. for 30 minutes, then fixed and stained with goat-anti-mouse Ig, there was a lack of detectable monoclonal antibody mAb 4, shown in FIG. 2C, in contrast to the mAb4 binding seen in FIG. 2A. The lack of detectable mAb4 on the membrane was due to BCRC internalization. When the CRL 1648 cells were incubated with mAb 4 at 37° C. for 15 minutes, then fixed and stained with goat-anti-mouse Ig, internalization was incomplete and residual bound monoclonal antibody mAb 4 was seen in FIG. 2D. When CRL 1648 cells were incubated with monoclonal antibody mAb 4 at 37° C. for 30 minutes, then fixed and stained with goat-anti-hu-IgM, BCRC was not detectable, which is shown in FIG. 2E.

Example 10

Inhibition of mAb 4 Binding by Pretreated B Cell Lines with or without Acid Wash Assessment of mAb Induced Internalization of mIgM To determine relative cell surface mIgM levels under various conditions, B-cell lines were either exposed to glutaraldehyde-fixed cells (rows 1 and 2 in Table 19) (as per SEM protocol below) or viable cells were used. Cells were exposed to mAb 4, 10 mcgs/ml at 4° C. for 0 minutes (rows 3 and 4 in Table 19), and for 5 minutes (rows 5 and 6 in Table 19), 15 minutes (rows 7 and 8 in Table 19), or 30 minutes (rows 9 and 10 in Table 19) at 37° C. Cells were then washed with pH 7.0 PBS or pH 4.0 0.5M acetate buffer 0.15 N NaCl prior to use in inhibition of mAb 4-HRP binding assays. Row 1 was set as 100% binding for each cell line and row 2 demonstrated acid wash ability to remove cell bound mAb 4 and allow mAb 4-HRP adsorption by cells reducing mAb 4-HRP available for binding assay. Similar results were seen for cells incubated on ice, indicating that both glutaraldehyde fixation and cold reduce mAb mediated internalization of mIgM. Timed experiments demonstrated that by 30 min at 37° C., cell inhibition is reduced without a difference between PBS and acetate wash (pH 4.0), suggesting that mIgM is predominantly internalized. The results are presented in Table 19 below.

TABLE 19

| Cell Inhibition of mAb 4-HRP binding to target with | Cell Treatment prior to adsorption | CRL 1648 | CRL 1647 | CRL 1596 |
|---|---|---|---|---|
| Glutaraldehyde-Fixed | PBS | 100 | 100 | 100 |
| Glutaraldehyde-Fixed | Acetate | 10 | 21 | 19 |
| Live cells on Ice | PBS | 92 | 95 | 88 |
| Live cells on Ice | Acetate | 12 | 18 | 20 |
| Live 37° (5 min) | PBS | 77 | 67 | 66 |
| Live 37° (5 min) | Acetate | 26 | 18 | 27 |
| Live 37° (15 min) | PBS | 78 | 81 | 72 |
| Live 37° (15 min) | Acetate | 48 | 44 | 56 |
| Live 37° (30 min) | PBS | 70 | 64 | 60 |
| Live 37° (30 min) | Acetate | 66 | 62 | 61 |

Example 11

Biologic Activity mAb4-2b Mediates Growth Inhibition, Anti-Clonogenic Activity and Apoptosis Due to the uniqueness of the sequences in the mIgM PD and evidence that trans-membrane cell signaling is conveyed to CD79αβ, examining growth curves (MTT) and clonogenicity of CA 46 (CRL 1648) cells was done to determine whether there is a modulation of this process (Kikushige Y, et al., Cancer Cell 20(2):246-59 (2011); Martinez-Climent J A, Haematol 95(2): 293-302 (2010); Franken N P, et al., Nature Protocols 1:2315-2319 (2006)). Initial testing for single clone survival at limiting dilution in 96 well plates indicated that three of the monoclonal antibodies had some activity. The strongest activity was with the monoclonal antibody mAb4-2b that binds in both the PD and Domain 4 and to a conformational epitope region. Monoclonal antibody mAb4-2b binds to a partially detergent sensitive, paraformaldehyde and a reduction resistant epitope. The other 3 mAbs bind to more proximal epitopes in the PD. Whether these cell growth inhibitory effects are related to blocking epitopes directly transmitting signaling or are steric-related due to the large size of the mAb and/or to micro-clustering is unclear.

Overall, as shown in the inhibition assays below in Tables 20 to 23, the most potent mAb, mAb4-2b, reduced CA 46 clonogenic capacity 100 fold (Kikushige Y, et al., Cancer Cell 20(2):246-59 (2011); Martinez-Climent J A, Haematol 95(2): 293-302 (2010); Franken N P, et al., Nature Protocols 1:2315-2319 (2006)).

Inhibition Assays

Cells are plated in 24 well plates and transferred to 96 well plates with 1:2 serial dilutions as indicated below in Tables 20 to 23. The MTT assay is carried out, where each value is the average of 8 wells per dilution point. ng=no grown, no viable cells

TABLE 20

| CA 46 (CRL 1648) | | | | | | | | | | | | |
|---|---|---|---|---|---|---|---|---|---|---|---|---|
| # cells/well | 5000 | 2500 | 1250 | 0625 | 0312 | 0156 | 0078 | 0039 | 0019 | 0008 | 0004 | 000 |
| mAb4-2b | 2.6 | 1.3 | 0.9 | 0.7 | ng | ng | Ng | ng | ng | ng | ng | ng |
| Control | 4.0 | 4.0 | 4.0 | 2.7 | 1.9 | 1.6 | 0.9 | 0.6 | 04 | 0.4 | ng | ng |
| Visual confirmation | | | | + | + | + | + | + | + | + | + | + |

TABLE 21

| SU-DHL-5 (CRL 2958) | | | | | | | | | | | | |
|---|---|---|---|---|---|---|---|---|---|---|---|---|
| # cells/well | 5000 | 2500 | 1250 | 0625 | 0312 | 0156 | 0078 | 0039 | 0019 | 0008 | 0004 | 000 |
| mAb4-2b | 2.0 | 1.1 | 0.7 | 0.4 | ng | ng | ng | ng | ng | ng | ng | ng |
| Control | 4.0 | 4.0 | 4.0 | 3.7 | 2.9 | 1.9 | 0.9 | 0.6 | 0.4 | 0.4 | ng | ng |
| Visual confirmation | | | | | + | + | + | + | + | + | + | + |

TABLE 22

| Ramos (CRL 1596) | | | | | | | | | | | | |
|---|---|---|---|---|---|---|---|---|---|---|---|---|
| # cells/well | 5000 | 2500 | 1250 | 0625 | 0312 | 0156 | 0078 | 0039 | 0019 | 0008 | 0004 | 000 |
| mAb4-2b | 3.0 | 2.1 | 1.7 | 0.7 | 0.3 | ng | ng | ng | ng | ng | ng | ng |
| Control | 4.0 | 4.0 | 4.0 | 3.6 | 2.7 | 1.1 | 0.8 | 0.8 | 0.5 | 0.5 | 0.3 | ng |
| Visual confirmation | | | | | | + | + | + | + | + | + | + |

TABLE 23

| | Namalwa (CRL 1432) | | | | | | | | | | | |
|---|---|---|---|---|---|---|---|---|---|---|---|---|
| # cells/well | 5000 | 2500 | 1250 | 0625 | 0312 | 0156 | 0078 | 0039 | 0019 | 0008 | 0004 | 000 |
| mAb4-2b | 3.2 | 2.4 | 0.9 | 0.2 | ng | ng | ng | ng | ng | ng | ng | ng |
| Control | 4.0 | 4.0 | 4.0 | 4.0 | 2.6 | 1.0 | 0.8 | 0.8 | 0.5 | 0.5 | 0.3 | ng |
| Visual confirmation | | | | | + | + | + | + | + | + | + | + |

Example 12

Limiting Dilution Assays and Cell Density Experiments

Limiting dilution assays with or without 1 microgram of mAb 4 demonstrated significant cell survival and growth characteristics by day 10. The results are presented in Table 24 below. Values are presented as % viable cells of mAb 4 treated/% viable cells of control mAb treated. Note the significant difference in cell growth between the doubling of media volume between 48 and 24 cell culture plates. Cells were plated with 100 microliters in 96 well plates, 250 microliters in 48 well plates, and 500 microliters in 24 well plates. Marked inhibition of growth was observed up to 500-1000 cells plated. It is believed that this represents the effects on a paracrine growth factor produced by stem cell which are killed by mAb 4. These experiments also suggest that several distinct populations of stem cells exist in different frequencies capable of rescuing cell growth at different cell densities.

TABLE 24

| Cell Lines | 10 cells/ 96 well | 10 cells/ 48 well | 10 cells/ 24 well | 50 cells/ 96 well | 50 cells/ 48 cells | 50 cells/ 24 well |
|---|---|---|---|---|---|---|
| CRL 1648 | 32 | 21 | <1 | 67 | 25 | <1 |
| CRL 1647 | 41 | 18 | <1 | 57 | 28 | <1 |
| CRL 1596 | 36 | 23 | <1 | 66 | 18 | <1 |

Statistical analysis: Student's t-test was used to assess statistical validity of data points shown. All data points consist of 12 wells in each of 3 experiments performed, and representative average values are shown. The first analysis is represented by each data point comparing % viable cells of mAb 4 treated/% viable cells of control mAb treated. Each of the 18 data points shown reached statistical level of p<0.5. The second analysis demonstrated statistical differences between the 48 well viable cell counts and the 24 well paired for each cell line in comparison. These also exceeded p<0.5 in each case. In growth inhibition studies, MTT viability counts showed that inhibition was inversely proportional to the number of cells plated. Similar experiments on control mIgM−, mIgG+ expressing cells did not show any biologic effects and polyclonal rabbit or goat anti-IgM was not anti-clonogenic. This suggests that the specificity determining inhibition is located in neo-epitopes near the cell membrane.

Figure 6A:
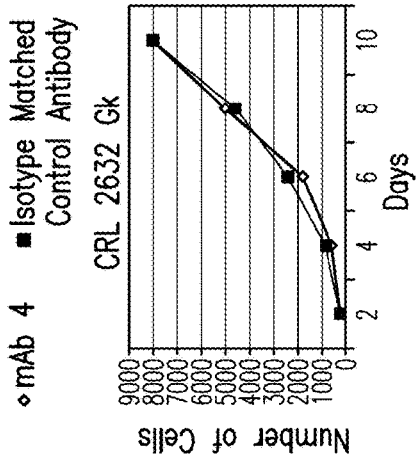
FIGS. 6A-6F.
Figure 6B:
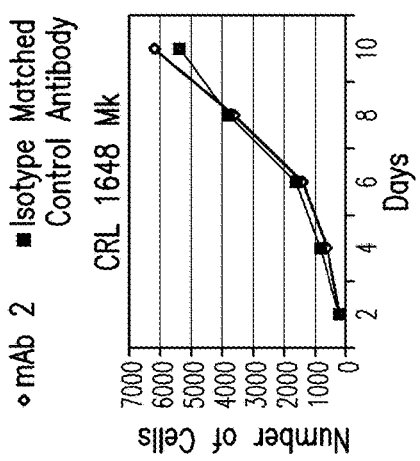
Figure 6C:
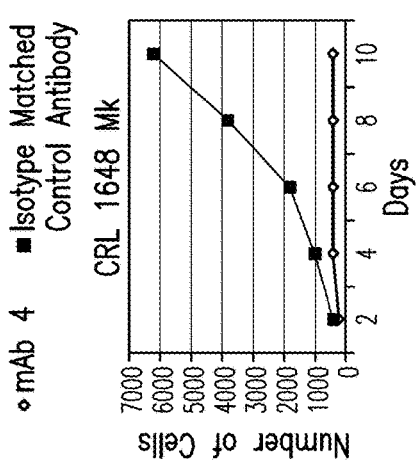
Figure 6D:
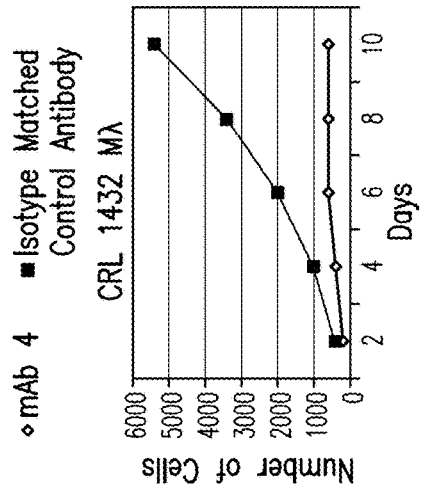
Figure 6E:
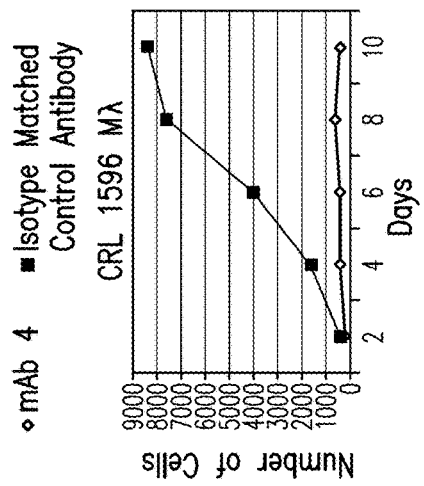
Figure 6F:
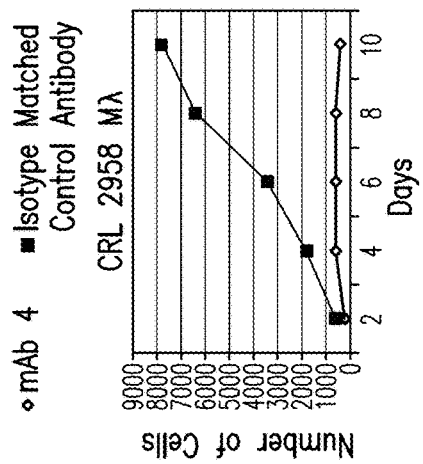

Growth curves: mIgM B-cell lines were grown in the presence of 1 μg/ml of mAb4-2b (as shown in Tables 20 to 23). Cells were plated at 20 cells/ml. Plates were collected every 2 days, with viable cells determined by MTT assay. Relative MTT OD was plotted for each time point. Apoptosis was scored by the absence of viable cells (Day 10) as determined by recloning cultures of surviving cells in the absence of antibody. The results are presented in FIGS. 6A-6F. Both the isotype-matched control antibody and the control anti-PD mAb 2 did not induce growth inhibition of the CRL 1648 cell line, shown in FIGS. 6A, 6B, and 6D-6F. When a control B-cell line expressing mIgG, CRL 2632, was used, mAb 4 did not bind to mIgG and did not suppress growth of this cell line, shown in FIG. 6C. FIGS. 6D-6F show that mAb 4 did induce growth inhibition of mIgM expressing B-cell lines CRL 1648, CRL 2958, CRL 1596 and CRL 1432.

Figure 7:
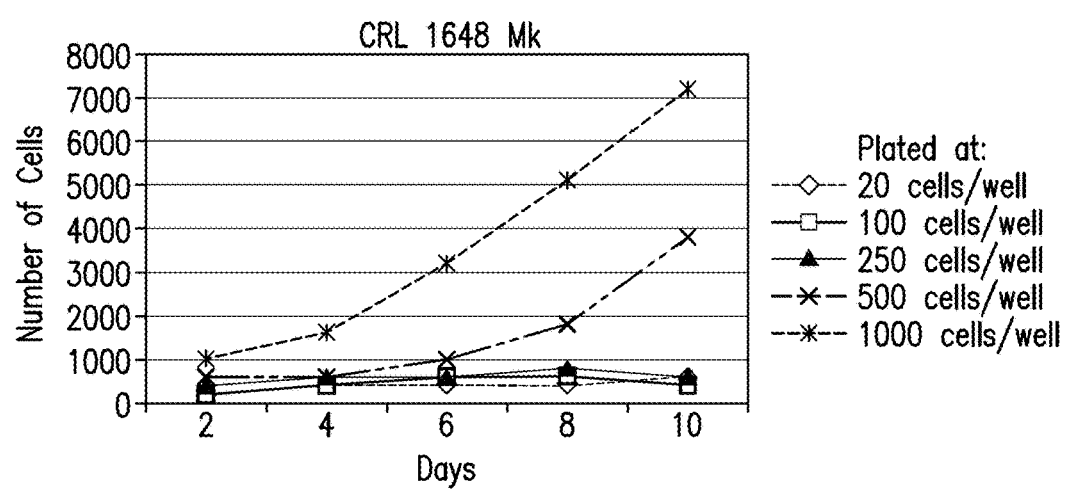
FIG. 7 is a graph showing the effect of monoclonal antibody mAb 4 on growth of mIgM-expressing B-cell line CRL 1648 at cell dilutions of 20 cells/well, 100 cells/well, 250 cells/well, 500 cells/well and 1,000 cells/well.

The inhibition of growth of mIgM-expressing B-cell line CRL 1648 by monoclonal antibody mAb 4 over ten days was tested at cell dilutions of 20 cells/well, 100 cells/well, 250 cells/well, 500 cells/well and 1,000 cells/well. As shown in FIG. 7, monoclonal antibody mAb 4 inhibited growth of mIgM expressing B-cell line CRL 1648 for a ten day period, but not when the concentration of cells plated was >500 cells/well.

Example 13

Complement Lysis and ADCC

The goal was to assess the immune cytotoxic capability of these monoclonal antibodies with regard to human complement (C') (IgG2, IgG3 and IgM) and human effector-cell mediated antibody directed cell-mediated cytotoxicity (ADCC) (IgG2 and IgG3) (Paneerselvam M, et al., J Immunol 136:2534-2541 (1986); Welt S, et al., Clin Immunol Immunopathol 45:214-229 (1987)). As these monoclonal antibodies are mouse monoclonal antibodies, this analysis was in part serving only to help determine if C' or ADCC was positive with these mouse antibodies and would therefore be an important factor to retain in clinical product development of humanized antibodies. While mouse IgG1 monoclonal antibodies may not have the capabilities of effector function due to their Ig sub-class, the focus is to determine if any individual clone has exceptional activity.

In the final analysis of isotypes collected from the clones of the final panel saved for further analysis based on initial binding studies were four IgG2b and two IgG1 monoclonal antibodies, which included anti-mIgM-mAb1-1, mAb2-2b, mAb3-2b, and mAb4-2b. None of these were positive in the assay as they were done at 37° C. and internalization occurred rapidly. As these results were a consequence of the rapid internalization, they are in sharp contrast with other antibodies binding to proximal domain epitopes that are reported to mediate these immune mechanisms. These results could also be due to low antigen levels, resistance factors or isotype (Paneerselvam M, et al., J Immunol 136:2534-2541 (1986); Welt S, et al., Clin Immunol Immunopathol 45:214-229 (1987)). Rituximab and polyclonal rabbit anti-human IgM were used as positive controls.

Pharmaceutical Formulations

Therapeutic formulations of a polypeptide or antibody may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"), i.e., buffering agents, stabilizing agents, preservatives, isotonifiers, non-ionic detergents, antioxidants, and other miscellaneous additives. See Remington's Pharmaceutical Sciences, 16th edition, Osol, Ed. (1980). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" may be added to ensure isotonicity of liquid compositions of the present invention and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stress without causing denaturation of the protein. Suitable non-ionic surfactants include polysorbates (20, 80, etc.), polyoxamers (184, 188 etc.), pluronic polyols, polyoxyethylene sorbitan monoethers (TWEEN®-20, TWEEN®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g., starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly/2-hydroxyethyl-methacrylate, poly (vinyl alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody, or fragment thereof which will be effective in the treatment of a particular disorder or condition will depend on the nature of the disorder or condition, and can be determined by standard clinical techniques. Where possible, it is desirable to determine the dose response curve and the pharmaceutical compositions of the invention first in vitro, and then in useful animal model systems prior to testing in humans.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary form once a month to daily depending on a number of clinical factors, including the type of disease, severity of disease, and the subject's sensitivity to the therapeutic agent.

Diagnostic Uses for Anti-B-Cell mIgM Antibodies

The antibodies of the invention include derivatives that are modified, i.e., by the covalent attachment of any type of molecule to the antibody, such that covalent attachment does not interfere with binding to B-cell mIgM. For example, but not by way of limitation, the antibody derivatives include antibodies that have been modified, e.g., by biotinylation, HRP, or any other detectable moiety.

Antibodies of the present invention may be used, for example, but not limited to, to purify or detect BCRC, including both in vitro and in vivo diagnostic methods. For example, the antibodies have use in immunoassays for qualitatively and quantitatively measuring levels of BCRC in biological samples. See, e.g., Harlow, et al., Antibodies: A Laboratory Manual, Cold Spring Harbor Laboratory Press, 2nd ed. (1988), which is incorporated by reference herein in its entirety.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays.

The present invention further encompasses antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Techniques for conjugating enzymes to antibodies are described in O'Sullivan, et al., "Methods for the Preparation of Enzyme-Antibody Conjugates for Use in Enzyme Immunoassay," in Methods in Enzymology, Langone, et al., eds. pp. 147-66, Academic Press (1981). See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digloxin) and one of the different types of labels mentioned above is conjugated with an anti-hapten antibody (e.g., anti-digloxin antibody). Thus, indirect conjugation of the label with the antibody can be achieved.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. See Zola, Monoclonal Antibodies: A Manual of Techniques, pp. 147-158. CRC Press (1987).

Competitive binding assays rely on the ability of a labeled standard to compete with the test sample for binding with a limited amount of antibody. The amount of target in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Antibodies may be attached to solid supports, which are particularly useful for immunoassays or purification of the target antigen. Such solid supports include, but are not limited to, glass, cellulose, polyacrylamide, nylon, polystyrene, polyvinyl chloride or polypropylene. In this process, the antibodies are immobilized on a solid support such as SEPHADEX™ resin or filter paper, using methods well known in the art. The immobilized antibodies are contacted with a sample containing the target to be purified, and thereafter the support is washed with a suitable solvent that will remove substantially all the material in the sample except the target to be purified, which is bound to the immobilized antibodies. Finally, the support is washed with another suitable solvent, such as glycine buffer, that will release the target from the antibodies.

Labeled antibodies, and derivatives and analogs thereof, that specifically bind to B-cell mIgM can be used for diagnostic purposes to detect, diagnose, or monitor diseases, disorders, and/or conditions associated with the aberrant expression and/or activity of B-cell malignancies. The invention provides for the detection of aberrant expression of B-cell mIgM, comprising (a) assaying the expression of B-cell mIgM in cells or body fluid of an individual using one or more antibodies of the present invention specific to B-cell mIgM and (b) comparing the level of gene expression with a standard gene expression level, whereby an increase or decrease in the assayed B-cell mIgM expression level compared to the standard expression level is indicative of aberrant expression.

Antibodies may be used for detecting the presence and/or levels of B-cell mIgM in a sample, e.g., a bodily fluid or tissue sample. The detecting method may comprise contacting the sample with a B-cell mIgM antibody and determining the amount of antibody that is bound to the sample. For immunohistochemistry, the sample may be fresh or frozen or may be embedded in paraffin and fixed with a preservative such as formalin, for example.

The invention provides a diagnostic assay for diagnosing a disorder, comprising (a) assaying the expression of B-cell mIgM in B cells or body fluid of an individual using one or more antibodies of the present invention and (b) comparing the level of gene expression with a standard gene expression level, whereby an increase or decrease in the assayed gene expression level compared to the standard expression level is indicative of a particular disorder.

Antibodies of the invention can be used to assay protein levels in a biological sample using classical immunohistological methods known to those of skill in the art (see, e.g., Jalkanen, et al., J Cell Biol 101:976 (1985); Jalkanen, et al., J Cell Biol 105:3087 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{121}$I), carbon ($^{14}$C), sulfur ($^{35}$S), tritium ($^{3}$H), indium ($^{112}$In, $^{111}$In), and technetium ($^{99}$Tc); luminescent labels, such as luminol; and fluorescent labels, such as fluorescein, rhodamine, and biotin. Radioisotope-bound isotopes may be localized using immunoscintiography.

One aspect of the invention is the detection and diagnosis of a disease or disorder associated with aberrant expression of B-cell mIgM in an animal, preferably a mammal and most preferably a human. In one embodiment, diagnosis comprises: a) administering (for example, parenterally, subcutaneously, or intraperitoneally) to a subject an effective amount of a labeled molecule which specifically binds to B-cell mIgM; b) waiting for a time interval following the administration permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of B-cell mIgM. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo imaging is described in Burchiel, et al., "Immunopharmacokinetics of Radiolabeled Antibodies and Their Fragments." Chapter 13 in Tumor Imaging: The Radiochemical Detection of Cancer, Burchiel, et al., eds., Masson Publishing (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours, 6 to 24 hours, or 6 to 12 hours. In another embodiment, the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

In another aspect, the present invention provides a method for diagnosing whether a patient has a B-cell lymphoma or leukemia by testing for the presence of B-cell mIgM in certain patient cells or body fluids. In one embodiment, the method comprises collecting a cell or body fluid sample from a subject, analyzing the body fluid for the presence of B-cell mIgM, comparing the amount to a defined or tested level established for normal cell or bodily fluid and determining if a patient has a B-cell lymphoma or leukemia based upon the level of expression of B-cell mIgM in the body fluid. The defined level of B-cell mIgM may be a known amount based upon literature values or may be determined in advance by measuring the amount in normal cell or body fluids. Specifically, determination of B-cell mIgM levels in certain body fluids permits specific and early, preferably before disease occurs, detection of diseases in the patient. Diseases that can be diagnosed using the present method include, but are not limited to, B-cell malignancies described herein. In the preferred embodiment, the body fluid is peripheral blood or peripheral blood leukocytes.

The antibody of the present invention can be provided in a kit, i.e., packaged combination of reagents in predetermined amounts with instructions for performing the diagnostic assay. Where the antibody is labeled with an enzyme, the kit may include substrates and cofactors required by the enzyme (e.g., a substrate precursor which provides the detectable chromophore or fluorophore). In addition, other additives may be included, such as stabilizers, buffers (e.g., a block buffer or lysis buffer), and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic Uses of Anti-B-Cell mIgM Antibodies

It is contemplated that the antibodies of the present invention may be used to treat a mammal. In one embodiment, the antibody is administered to a nonhuman mammal for the purposes of obtaining preclinical data, for example. Exemplary nonhuman mammals to be treated include non-human primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

An antibody, with or without a therapeutic moiety conjugated to it, administered alone or in combination with cytotoxic factor(s) can be used as a therapeutic. The present invention is directed to antibody-based therapies which involve administering antibodies of the invention to an animal, a mammal, or a human, for treating a B-cell lymphoma or leukemia. The animal or subject may be an animal in need of a particular treatment, such as an animal having been diagnosed with a particular disorder, e.g., one relating to B-cell lymphomas or leukemias. Antibodies directed against B-cell mIgM are useful for B-cell lymphomas or leukemias in animals, including but not limited to cows, pigs, horses, chickens, cats, dogs, non-human primates etc., as well as humans. For example, by administering a therapeutically acceptable dose of an antibody, or antibodies, of the present invention, or a cocktail of antibodies of the present invention, or in combination with other antibodies of varying sources, disease symptoms may be reduced or eliminated in the treated mammal.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit, or prevent diseases, disorders, or conditions associated with aberrant expression and/or activity of B-cell mIgM, including, but not limited to, any one or more of the diseases, disorders, or conditions described herein. The treatment and/or prevention of diseases, disorders, or conditions associated with aberrant expression and/or activity of B-cell mIgM includes, but is not limited to, alleviating at least one of the symptoms associated with those diseases, disorders, or conditions. Antibodies of the present invention may be provided in pharmaceutically acceptable compositions as known in the art or as described herein.

Anti-B-cell mIgM antibodies of the present invention may be used therapeutically in a variety of diseases. The present invention provides a method for preventing or treating B-cell malignancy diseases in a mammal. The method comprises administering a disease preventing or treating amount of anti-B-cell mIgM antibody to the mammal. The anti-B-cell mIgM antibody binds to B-cell mIgM and inhibits cell growth and induces apoptosis.

The amount of the antibody which will be effective in the treatment, inhibition, and prevention of a disease or disorder associated with aberrant expression and/or activity of B-cell mIgM can be determined by standard clinical techniques. The dosage will depend on the type of disease to be treated, the severity and course of the disease, whether the antibody is administered for preventive or therapeutic purposes, previous therapy, the patient's clinical history and response to the antibody, and the discretion of the attending physician. The antibody can be administered in treatment regimens consistent with the disease, e.g., a single or a few doses over one to several days to ameliorate a disease state or periodic doses over an extended time to prevent allergy or asthma. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems.

For antibodies, the dosage administered to a patient is typically 0.1 mg/kg to 150 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen for an anti-LFA-1 or anti-ICAM-1 antibody is disclosed in PCT Publication No. WO 94/04188.

The antibodies of the present invention, which may be in the form of a composition, should be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody composition to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

The antibodies of this invention may be advantageously utilized in combination with other monoclonal or chimeric antibodies, or with lymphokines or hematopoietic growth factors (such as, e.g., IL-2, IL-3 IL-7, and IFN-γ), for example, which serve to increase the number or activity of effector cells which interact with the antibodies.

The antibodies of the invention may be administered alone or in combination with other types of treatments, such as immunotherapy, chemotherapy, and radioisotopes.

In a preferred aspect, the antibody is substantially purified (e.g., substantially free from substances that limit its effect or produce undesired side effects). Various delivery systems are known and can be used to administer an antibody of the present invention, including injection, e.g., encapsulation in liposomes, microparticles, microcapsules, recombinant cells capable of expressing the compound, receptor-mediated endocytosis (see, e.g., Wu, et al., J Biol Chem 262:4429 (1987)), construction of a nucleic acid as part of a retroviral or other vector, etc.

The anti-B-cell mIgM antibody can be administered to the mammal in any acceptable manner. Methods of introduction include, but are not limited to, parenteral, subcutaneous, intraperitoneal, intrapulmonary, intranasal, epidural, inhalation, and oral routes, and if desired for immunosuppressive treatment, intralesional administration. Parenteral infusions include intramuscular, intradermal, intravenous, intra-arterial, or intraperitoneal administration. The antibodies or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection: intraventricular injection may be facilitated by an intraventricular catheter, for example, attached to a reservoir, such as an Ommaya reservoir. In addition, the antibody is suitably administered by pulse infusion, particularly with declining doses of the antibody. Preferably, the dosing is given by injections, most preferably intravenous or subcutaneous injections, depending in part on whether the administration is brief or chronic.

Pulmonary administration can also be employed, e.g., by use of an inhaler or nebulizer, and formulation with an aerosolizing agent. The antibody may also be administered into the lungs of a patient in the form of a dry powder composition (See, e.g., U.S. Pat. No. 6,514,496).

In a specific embodiment, it may be desirable to administer the therapeutic antibodies or compositions of the invention locally to the area in need of treatment. This may be achieved by, for example, and not by way of limitation, local infusion, topical application, by injection, by means of a catheter, by means of a suppository, or by means of an implant, the implant being of a porous, non-porous, or gelatinous material, including membranes, such as sialastic membranes, or fibers. Preferably, when administering an antibody of the invention, care must be taken to use materials to which the protein does not absorb.

In another embodiment, the antibody can be delivered in a vesicle, in particular, a liposome (see Langer, Science 249:1527 (1990); Treat, et al., Liposomes in the Therapy of Infectious Disease and Cancer, Lopez-Berestein, et al., eds., pp. 353-365 (1989); Lopez-Berestein, ibid., pp. 317-27; see generally, ibid.).

In yet another embodiment, the antibody can be delivered in a controlled release system. In one embodiment, a pump may be used (see Langer, Science 249:1527 (1990); Sefton, CRC Crit Ref Biomed Eng 14:201 (1987); Buchwald, et al., Surgery 88:507 (1980); Saudek, et al., N Engl J Med 321:574 (1989)). In another embodiment, polymeric materials can be used (see Medical Applications of Controlled Release, Langer, et al., eds., CRC Press (1974); Controlled Drug Bioavailability, Drug Product Design and Performance, Smolen, et al., eds., Wiley (1984); Ranger, et al., J Macromol Sci Rev Macromol Chem 23:61 (1983); see also, Levy, et al., Science 228:190 (1985); During, et al., Ann Neurol 25:351 (1989); Howard, et al., J Neurosurg 71:105 (1989)). In yet another embodiment, a controlled release system can be placed in proximity of the therapeutic target.

The present invention also provides pharmaceutical compositions. Such compositions comprise a therapeutically effective amount of the antibody and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable, or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In addition, the antibodies of the present invention may be conjugated to various effector molecules such as heterologous polypeptides, drugs, radionucleotides, carbohydrates, nucleotides, which include microRNA, and DNA synthetic nucleotides, or toxins. See, e.g., PCT Publication Nos. WO 92/08495; WO 91/14438; WO 89/12624; U.S. Pat. No. 5,314,995; and European App. No. EP 396,387. An antibody or fragment thereof may be conjugated to a therapeutic moiety such as a cytotoxin (e.g., a cytostatic or cytocidal agent), a therapeutic agent, or a radioactive metal ion (e.g., alpha-emitters such as, for example, 213Bi). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine) and highly toxic drugs (e.g., calicheamicin).

Techniques for conjugating such therapeutic moieties to antibodies are well known, see, e.g., Arnon, et al., "Monoclonal Antibodies For Immunotargeting Of Drugs In Cancer Therapy", in Monoclonal Antibodies and Cancer Therapy, Reisfeld, et al. (eds.), pp. 243-56 Alan R. Liss (1985); Hellstrom, et al., "Antibodies For Drug Delivery", in Controlled Drug Delivery, 2nd ed., Robinson, et al., eds., pp. 623-53, Marcel Dekker (1987); Thorpe, "Antibody Carriers Of Cytotoxic Agents In Cancer Therapy: A Review," in Monoclonal Antibodies '84: Biological And Clinical Applications, Pinchera, et al., eds., pp. 475-506 (1985); "Analysis, Results, And Future Prospective Of The Therapeutic Use Of Radiolabeled Antibody In Cancer Therapy," in Monoclonal Antibodies For Cancer Detection and Therapy, Baldwin, et al., eds., pp. 303-16. Academic Press (1985); and Thorpe, et al., Immunol Rev 62:119 (1982). Alternatively, an antibody can be conjugated to a second antibody to form an antibody heteroconjugate. See, e.g., U.S. Pat. No. 4,676,980.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi, et al., Int Immunol, 6:1567 (1994)), VEGI (see, International Publication No. WO 99/23105); a thrombotic agent; an anti-angiogenic agent, e.g., angiostatin or endostatin; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Those skilled in the art will recognize, or be able to ascertain using no more than routine experimentation, many equivalents to the specific embodiments of the invention described herein. Such equivalents are intended to be encompassed by the following claims.

The invention claimed is:

1. A method of killing or inhibiting the growth of B cells in a subject, comprising administering an effective amount of a monoclonal antibody or antigen binding fragment thereof that specifically binds to membrane bound IgM of a B-cell Receptor Complex to a subject in need thereof, thereby killing or inhibiting the growth of the B cells in a subject, wherein the heavy chain variable region of the monoclonal antibody comprises the amino acid sequence of SEQ ID NO: 2 and the light chain variable region of the monoclonal antibody comprises the amino acid sequence of SEQ ID NO: 4.

2. A method of killing or inhibiting the growth of B cells in a subject, comprising administering an effective amount of a monoclonal antibody or antigen binding fragment thereof that specifically binds to membrane bound IgM of a B-cell Receptor Complex to a subject in need thereof, thereby killing or inhibiting the growth of the B cells in a subject, wherein the heavy chain variable region (VH) of the monoclonal antibody comprises:
   (a) a heavy chain variable region CDR1 comprising the amino acid sequence of SEQ ID NO: 5;
   (b) a heavy chain variable region CDR2 comprising the amino acid sequence of SEQ ID NO: 6;
   (c) a heavy chain variable region CDR3 comprising the amino acid sequence of SEQ ID NO: 7; and
   wherein the light chain variable region (LH) of the monoclonal antibody comprises:
   (d) a light chain variable region CDR1 comprising the amino acid sequence of SEQ ID NO: 8;
   (e) a light chain variable region CDR2 comprising the amino acid sequence of SEQ ID NO: 9; and
   (f) a light chain variable region CDR3 comprising the amino acid sequence of SEQ ID NO: 10.

3. The method of claim 1, wherein the monoclonal antibody comprises a heavy chain variable region (VH) encoded by the nucleic acid sequence of SEQ ID NO: 1 and a light chain variable region (VL) encoded by the nucleic acid sequence of SEQ ID NO: 3.

4. The method of claim 1, wherein the monoclonal antibody is conjugated to a cytotoxin, radioisotope or immunotoxin.

5. A method of producing an antibody or antigen binding fragment thereof, comprising:
   a. culturing a host cell comprising an expression vector, wherein the expression vector comprises a recombinant nucleic acid comprising the nucleic acid sequences of SEQ ID NO: 1 and SEQ ID NO: 3, in culture medium under conditions wherein the nucleic acid sequence is expressed, thereby producing a polypeptide comprising light and heavy chain variable regions; and
   b. recovering the polypeptide from the host cell or culture medium.

6. A method for purifying membrane bound IgM (mIgM) of a B-cell Receptor Complex in a sample comprising (a) attaching monoclonal antibodies designated mAb1-1 produced by a hybridoma cell line from fusion 117 (ATCC deposit number PTA-121719) alone or in combination with monoclonal antibodies designated mAb2-2b produced by a hybridoma cell line from fusion 118 (ATCC deposit number PTA-121717) and monoclonal antibodies designated mAb3-2b produced by a hybridoma cell line from fusion 118 (ATCC deposit number PTA-121718) to a solid support; (b) contacting the immobilized antibodies with the sample; (c) washing the solid support with a first solvent to remove substantially all the material in the sample except the mIgM of the B-cell Receptor Complex that is bound to the immobilized antibodies; and (d) washing the solid support with a second solvent to release the mIgM of the B-cell Receptor Complex from the immobilized antibodies.

7. The method of claim 1, wherein the effective amount of the monoclonal antibody is administered to a subject in need thereof in combination with one or more anti-B-cell antibodies, a cytotoxin, and/or a radioisotope, thereby killing or inhibiting the growth of the B cells in a subject.

* * * * *

SEQUENCE LISTING

<160> NUMBER OF SEQ ID NOS: 18

<210> SEQ ID NO 1
<211> LENGTH: 447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaccaggcat cccagggtca ccatggagtt agtttgggca gcagatccag gggccagtgg      60
atagacagat gggggtgtcg tttggctga ggagacggtg actgaggttc cttgacccca     120
gtagtccata ccatagttac ccctcgttct gcacagtaa tagaccgcag agtcctcaga     180
tgtcaggctg ctgagttgca gtaggctgt gctggaggat ttgtctacag tcagtgtggc     240
cttggtcttg aacttctcat tgtagttagt actaccacta ttaggatgaa ttattcctat    300
ccactcaagg ccttgtccag gcctctgctt cacccagttc atccagtagc tggtgaaagt    360
gtagccagaa gccttacagg acaacttcag tgaagcccca ggcttaccag gctcagcccc    420
agactcctgc agcttgacct ccggaag                                        447

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Glu Glu Ser Gly Ala Glu Leu Val Lys Pro Gly Ala
1               5                   10                  15

Ser Leu Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Ile Ile His Pro Asn Ser Gly Ser Thr Asn Tyr Asn Glu Lys Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Thr Arg Gly Asn Tyr Gly Met Asp Tyr Trp Gly Gln Gly Thr
            100                 105                 110

Ser Val Thr Val Ser Ser
        115

<210> SEQ ID NO 3
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
taactgctca ctggatggtg ggaagatgga tacagttggt gcagcatcag cccgtttcag      60
ctccagcttg gtcccagcac cgaacgtgag cggaggaata ctaaaatgtt gctgacagta    120

-continued

```
ataaactgcc aggtcttcag cctgcacact gctgatggtg aaagtgaaat ccgtcccaga    180
tccactgcca gtgaagcgat cagggactcc agtgttccgg taggatgccg agtaaatcag    240
taatgtagga gattgtcctg gtttctgttg ataccaggct acagcagtac tcacatcctg    300
actggccttg caggtgatgc tgaccctgtc tcctactgag gtggacatga atttgtgaga    360
ctgggtcatc acaatgtccc                                               380
```

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Thr Leu Leu Ile
        35                  40                  45

Tyr Ser Ala Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Phe Ser Ile Pro Pro
                85                  90                  95

Leu Thr Phe Gly Ala Gly Thr Lys Leu Glu Leu Lys Arg Ala
            100                 105                 110
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Tyr Thr Phe Thr Ser Tyr Trp
1               5
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ile His Pro Asn Ser Gly Ser Thr
1               5
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Tyr Cys Ala Arg
1

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Ser Tyr Arg Asn Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln His Phe Ser Ile Pro Pro Leu Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Gly Glu Val Ser Ala Asp Glu Glu Gly Phe Glu Asn
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Leu Gln Leu Glu Glu Ser Cys Ala Glu Ala Gln Asp Gly Glu Leu
1               5                   10                  15

Asp Gly

<210> SEQ ID NO 13
```

```
<211> LENGTH: 12
<212> TYPE: PRT
<213> ORGANISM: Homo sapiens

<400> SEQUENCE: 13

Glu Gly Glu Val Ser Glu Asp Glu Glu Gly Phe Glu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Gly Glu Asn Ser Ala Asp Glu Glu Gly Phe Glu Asn
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Gly Glu Val Ser Glu Asp Glu Glu Gly Phe Glu Asn
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Gly Glu Val Ser Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Glu Gly Phe Glu Asn
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5
```